(12) United States Patent
Berkman

(10) Patent No.: US 7,696,185 B2
(45) Date of Patent: Apr. 13, 2010

(54) PEPTIDOMIMETIC INHIBITORS OF PSMA, COMPOUNDS COMPRISING THEM, AND METHODS OF USE

(75) Inventor: Cliff Berkman, San Francisco, CA (US)

(73) Assignee: Cancer Targered Technology LLC, San Francisco, CA (US)

( * ) Notice: Subject to any disclaimer, the term of this patent is extended or adjusted under 35 U.S.C. 154(b) by 240 days.

(21) Appl. No.: 11/686,272

(22) Filed: Mar. 14, 2007

(65) Prior Publication Data

US 2007/0219165 A1 Sep. 20, 2007

Related U.S. Application Data

(60) Provisional application No. 60/782,211, filed on Mar. 14, 2006.

(51) Int. Cl.
*A61K 31/66* (2006.01)
*C07F 9/02* (2006.01)

(52) U.S. Cl. .................. 514/114; 558/169

(58) Field of Classification Search ............ 558/169; 514/114

See application file for complete search history.

(56) References Cited

U.S. PATENT DOCUMENTS 6,372,726 B1 * 4/2002 Slusher et al. ............ 514/75
2004/0110723 A1 6/2004 Frangioni

OTHER PUBLICATIONS

Maung et al., "Molecular pruning studies on a phosphoramidate gamma-diglutamate analog inhibitor of prostate-specific membrane antigen; optimizing the potency of phenethylphosphonamidate inhibitors of prostate-specific membrane antigen," 229th National Meeting of the American Chemical Society, vol. 229, Mar. 2005.
Tang et al., "Prostate targeting ligands based on N-acetylated alpha-linked acidic dipeptidase," Biochemical and Biophysical Research Communications, 307(1):8-14 (2003).
Maung et al., "Probing for a hydrophobic a binding register in prostate-specific membrane antigen with phenylalkylphosphonamidates," Bioorganic & Medicinal Chemistry, 12(18):4969-4679 (2004).
Chen et al., "N-Phosphoryl Amino Acids and Peptides: Part V: O-Alkyl Substitution Effects on the 31P-NMR Spectra of Phosphoramidates," Phosphorus, Sulfur and Silicon, 61:31-39 (1991).
Li et al., "Beta-Carboxyl Catalytic Effect of N-Phosphoryl Aspartic Acid," Bioorganic Chemistry, 20:285-295 (1992).
Ng et al., "Synthesis of phosphoramidate and phosphoramidothionate inhibitors of prostate specific membrane antigen," 220th National Meeting of the American Chemical Society, 220, Aug. 2000.
Etreby et al., "Induction of Apoptosis by Mifepristone and Tamoxifen in Human LNCaP Prostate Cancer Cells in Culture," The Prostrate, 43(1):31-42 (2000).
Rodriguez et al., "Inhibition of Glutamate Carboxypeptidase II by Phosphonamidothionate Derivates of Glutamic Acid," 16(4): 359-365 (2001).
Wone et al., "Optimizing phenylethylphosphonamidates for the inhibition of prostate-specific membrane antigen," Bioorganic & Medicinal Chemistry, 14(1):67-76 (2006).
Tino et al., "Isolation and characterization of monoclonal antibodies specific for protein conformational epitopes present in prostate-specific membrane antigen (PSMA)," Hybridoma, 19(3):249-257 (2000).
Barren et al., "Monoclonal Antibody 7E11.C5 Staining of Viable LNCAP Cells," Prostate, 30(1):65-68 (1997).
Stefanic et al., "Aspartate and Glutamate Mimetic Structures in Biologically Active Compounds," Current Medicinal Chemistry, 11, 945-968 (2004).

* cited by examiner

*Primary Examiner*—Rei-tsang Shiao
(74) *Attorney, Agent, or Firm*—McDonnell Boehnen Hulbert & Berghoff, LLP

(57) ABSTRACT

Compounds of the formula, A—L—B, wherein A is glutamate or a glutamate analog; L is a phosphoramidate or a phosphoramidate analog; and B is serine or a serine analog are described which are potent inhibitors of prostate-specific membrane antigen (PMSA). Such compounds are useful in treatment of prostate cancer; and when chemically attached to a fluorescent dye, can efficiently and selectively label prostate cancer cells for fluorescent imaging.

20 Claims, 12 Drawing Sheets

PEPTIDOMIMETIC INHIBITORS OF PSMA, COMPOUNDS COMPRISING THEM, AND METHODS OF USE

CROSS-REFERENCE TO RELATED APPLICATIONS

This application claims the benefit of priority of U.S. Provisional Application 60/782,211, filed Mar. 14, 2006, which is hereby incorporated by reference in its entirety.

STATEMENT OF GOVERNMENT SUPPORT

The U.S. Government has a paid-up license in this invention and the right in limited circumstances to require the patent owner to license others on reasonable terms as provided for by the terms of Grant Nos. 2 S06 GM52588-04 and 2 S06 GM52588-08, each awarded by the National Institutes of Health; Grant No. 1 U56 CA96217-01, awarded by the National Cancer Institute; and Grant No. PC051060, awarded by the Department of Defense.

BACKGROUND OF THE INVENTION

1. Field of the Invention

The present invention relates to small molecules having high affinity and specificity to prostate-specific membrane antigen (PSMA) and methods of using them for diagnostic and therapeutic purposes.

2. Summary of the Related Art

Prostate-specific membrane antigen (PSMA) is uniquely overexpressed on the surface of prostate cancer cells as well as in the neovasculature of a variety of solid tumors. As a result, PSMA has attracted attention as a clinical biomarker for detection and management of prostate cancer. Generally, these approaches utilize an antibody specifically targeted at PSMA to direct imaging or therapeutic agents. For example, ProstaScint (Cytogen, Philadelphia, Pa.), which has been approved by the FDA for the detection and imaging of prostate cancer, utilizes an antibody to deliver a chelated radioisotope (Indium-111). However, it is now recognized that the ProstaScint technology is limited to the detection of dead cells and therefore its clinical relevance is questionable.

The success of cancer diagnosis and therapy using antibodies is limited by challenges such as slow elimination of these biomolecules from the blood and poor vascular permeability. In addition, large antibodies bound to cell-surface targets present a barrier for subsequent binding of additional antibodies at neighboring cell-surface sites resulting in a decreased cell-surface labeling.

In addition to serving as a cell-surface target for antibodies delivering diagnostic or therapeutic agents, a largely overlooked and unique property of PSMA is its enzymatic activity. That is, PSMA is capable of recognizing and processing molecules as small as dipeptides. Despite the existence of this property, it has been largely unexplored in terms of the development of novel diagnostic and therapeutic strategies. There are a few recent examples in the literature that have described results in detecting prostate cancer cells using labeled small-molecule inhibitors of PSMA.

SUMMARY OF THE INVENTION

The present invention comprises compounds that bind to the prostate-specific membrane antigen (PSMA) with high affinity and specificity. Because of these properties, the compounds of the invention are useful for delivering diagnostic or therapeutic agents to cells presenting PSMA or to capture and detect such cells such as when the compounds of the invention are anchored directly or indirectly to a solid support. Concomitantly, therefore, the invention also comprises diagnostic methods for detecting and/or identifying cells presenting PSMA comprising contacting (or causing to be contacted) a cell suspected of presenting PSMA with a compound of the invention linked to a detectable marker or sensing device and determining whether the compound and cell are linked. The invention also comprises compositions comprising a compound of the invention together with a pharmaceutically acceptable carrier, excipient, and/or diluent. The invention further comprises methods of inhibiting or treating prostate cancer comprising administering to a patient having prostate cancer a therapeutically effective amount of a compound of the invention linked to a prostate cancer therapeutic agent (or a composition thereof).

The small molecules of the invention provide an advantage over approaches employing PMSA antibodies because preparation and purification of small molecules are more efficient and more cost effective than the preparation of antibodies.

DETAILED DESCRIPTION OF THE INVENTION

It has been recognized that tumor-targeting can be achieved by small molecules if they possess sufficient affinity for tumor cells. To be competitive with and substantially equivalent to antibody-based delivery agents, the affinity of small-molecules should be in the same range as that for antibodies to their targets.

Figure 1:
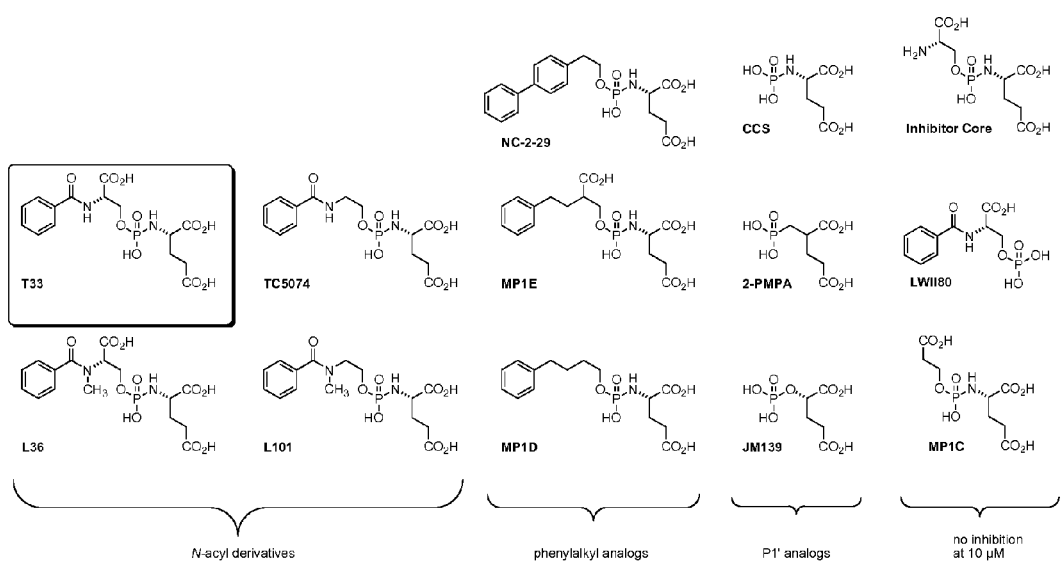
FIG. 1 displays molecular pruning analogs of T33.

In a first aspect, the invention comprises small molecules that target PSMA (preferably PSMA's enzymatic recognition site) that meet this criterion. A unique feature of the compounds of the invention is that they are primarily derived from a central phosphoramidate core. Specifically, such chemical compounds include all the compounds that are shown in FIG. 1 (except CCS, JM139, and 2-PMPA), FIG. 2 and FIGS. 7-12. The compounds of the invention generally have $IC_{50}$ of less than 5 μM, preferably less than 1 μM, and more preferably less than 100 nM, as measured according to the assay described in the Examples (vide infra).

The compounds of the invention have three components that result in a potent peptidomimetic inhibitor of PMSA that can also be functionalized to deliver a diagnostic or therapeutic agent to PSMA-expressing cells: 1) glutamate or a glutamate analog in the P1' position, 2) a central phosphoramidate or phosphoramidate analog as a zinc-binding group, and 3) a serine or serine analog in the P1 position connected through its side chain and preferably possessing a hydrophobic group on its N-terminus or N-terminus equivalent.

Accordingly, in an embodiment of the first aspect, the invention provides a compound of formula I:

  (I), wherein A is glutamate or a glutamate analog; L is a phosphoramidate or phosphoramidate analog; B is serine or a serine analog. Preferably the serine or serine analog possesses a hydrophobic group on its N-terminus or N-terminus equivalent. Pharmaceutically acceptable salts of all compounds of the invention disclosed in this specification are also an aspect of the invention.

In an preferred embodiment of the first aspect, the invention provides a compound of formula I wherein A is of the formula (Ia),

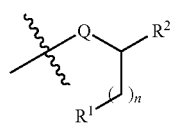  (Ia)

and pharmaceutically acceptable salts thereof, wherein n is 1, 2, 3, 4, 5 or 6;

Q is —O—, —S—, —N($R^3$)—, N($R^3$)O—, —ON($R^3$)—, —CH$_2$—, or =NO—, wherein Q is bonded to L;

$R^1$ and $R^2$ are independently —C(O)O$R^3$, —C(O)N($R^3$)$_2$, —P(O)(O$R^3$)$_2$, —OP(O)(O$R^3$)$_2$, —S(O)$_2$$R^3$, —S(O)$_2$O$R^3$, —S(O)$_2$N($R^3$)$_2$, or tetrazolyl;

and each independently —H or $C_1$-$C_6$ alkyl.

In another embodiment of the first aspect, the invention provides a compound of formula I wherein B is of the formula (Ib),

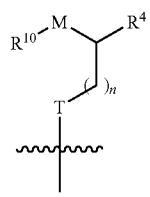  (Ib)

and pharmaceutically acceptable salts thereof, wherein n is 1, 2, 3, 4, 5 or 6;

$R^4$ is —H, —C(O)O$R^3$, —C(O)N($R^3$)$_2$, —P(O)(O$R^3$)$_2$, —OP(O)(O$R^3$)$_2$, —S(O)$_2$$R^3$, —S(O)$_2$O$R^3$, —S(O)$_2$N($R^3$)$_2$, or tetrazolyl;

M and T are independently —O—, —S—, —N($R^3$)—, or —CH$_2$—, wherein T is bonded to L;

$R^{10}$ is —H, —$C_1$-$C_6$ alkyl, aryl, —$C_1$-$C_6$ alkyl-aryl, -aryl-aryl, —X—$R^6$, —$R^7$, —C(O)$R^5$, —S(O)$_2$$R^5$, peptide, a dendrimer, or peptide dendrimer, wherein X is —O—, —S—, or —N($R^3$)—;

$R^5$ is —CH($R^{51}$)N($R^{52}$)$_2$;

$C_1$-$C_6$ alkyl optionally substituted with 1 to 3 groups which are independently -halogen, COO$R^{53}$, —N($R^{52}$)$_2$;

aryl;

or heteroaryl, wherein $R^{51}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —O$R^{53}$, —S$R^{53}$, —NH$_2$, —N(H)C(=NH)NH$_2$, —COO$R^{53}$, or —C(O)N($R^{53}$)$_2$; and $R^{52}$ is —H, $C_1$-$C_6$alkyl, —C(O)$R^{53}$, C(O)O$R^{53}$, —C(O)NH($C_1$-$C_6$alkyl), —C(O)N($R^{53}$)$_2$, —C(O)aryl, or —C(O)heteroaryl;

$R^{53}$ is —H, $C_1$-$C_6$alkyl, or $C_1$-$C_6$ alkyl-aryl;

$R^6$ is —H or $C_1$-$C_6$ alkyl; and $R^7$ is —$L^1$—$R^8$, wherein $L^1$ is —C(O)N($R^3$)—, —C(S)N($R^3$)—, —C(O)CH($R^{21}$)—, —C(O)(O), or —C(O)—$L^2$—, wherein $R^{21}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —O$R^{23}$, —S$R^{23}$, —NH$_2$, —N(H)C(=NH)NH$_2$, —COO$R^{23}$, or —C(O)N($R^{23}$)$_2$; and $R^{23}$ is —H, $C_1$-$C_6$alkyl, or $C_1$-$C_6$ alkyl-aryl;

$L^2$ is —$C_1$-$C_{24}$ alkyl- or -phenyl-$C_1$-$C_{24}$ alkyl-, wherein each alkyl group is optionally substituted with 1 to 4 groups which are oxo, =S, or —COOH; and one to six of the methylene groups in each alkyl group is optionally replaced by —O—, —S—, or —N($R^3$)—, provided that no two adjacent methylene groups are both replaced by —O—, —S—, or —N($R^3$)—; and $R^8$ is —H, —NH$_2$, or —OH;

and each $R^3$ is independently —H or $C_1$-$C_6$ alkyl.

In another embodiment of the first aspect, the invention provides a compound of formula I (and pharmaceutically acceptable salts thereof), wherein L is —P(O)(O$R^3$)—, —P(O)(N($R^3$)$_2$)—, —S(O)$_2$—, —C(O)—, or —C(S)—, wherein each $R^3$ is independently —H or $C_1$-$C_6$ alkyl.

In a preferred embodiment of the first aspect, the invention provides the compound of formula (II),

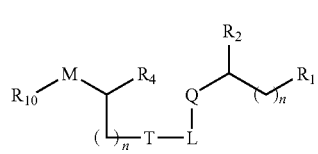  (II)

and pharmaceutically acceptable salts thereof, wherein each n is independently 1, 2, 3, 4, 5 or 6;

each $R^1$ and $R^2$ are independently —C(O)O$R^3$, —C(O)N($R^3$)$_2$, —P(O)(O$R^3$)$_2$, —OP(O)(O$R^3$)$_2$, —S(O)$_2$$R^3$, —S(O)$_2$O$R^3$, —S(O)$_2$N($R^3$)$_2$, or tetrazolyl;

each $R^3$ is independently —H or $C_1$-$C_6$ alkyl;

$R^4$ is —H, —C(O)$OR^3$, —C(O)N($R^3$)$_2$, —P(O)($OR^3$)$_2$, —OP(O)($OR^3$)$_2$, —S(O)$_2R^3$, —S(O)$_2OR^3$, —S(O)$_2$N($R^3$)$_2$, or tetrazolyl;

L is —P(O)($OR^3$)—, —P(O)(N($R^3$)$_2$)—, —S(O)$_2$—, —C(O)—, or —C(S)—;

M and T are independently —O—, —S—, —N($R^3$)—, or —CH$_2$—;

$R^{10}$ is —H, —C$_1$-C$_6$ alkyl, aryl, —C$_1$-C$_6$ alkyl-aryl, -aryl-aryl, —X—$R^6$, —$R^7$, —C(O)$R^5$, —S(O)$_2R^5$, a peptide, dendrimer, or peptide dendrimer wherein
  X is —O—, —S—, or —N($R^3$)—;
  $R^5$ is —CH($R^{51}$)N($R^{52}$)$_2$;
  $C_1$-$C_6$ alkyl optionally substituted with 1 to 3 groups which are independently -halogen, $COOR^{53}$, —N($R^{52}$)$_2$;
  aryl;
  or heteroaryl, wherein
    $R^{51}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —$OR^{53}$, —$SR^{53}$, —NH$_2$, —N(H)C(=NH)NH$_2$, —$COOR^{53}$, or —C(O)N($R^{53}$)$_2$; and
    $R^{52}$ is —H, $C_1$-$C_6$alkyl, —C(O)$R^{53}$, C(O)$OR^{53}$, —C(O)NH($C_1$-$C_6$alkyl), —C(O)N($R^{53}$)$_2$, —C(O)aryl, or —C(O)heteroaryl;
    $R^{53}$ is —H, $C_1$-$C_6$alkyl, or $C_1$-$C_6$ alkyl-aryl;
  $R^6$ is —H or $C_1$-$C_6$ alkyl;
  and
  $R^7$ is —$L^1$—$R^8$, wherein
    $L^1$ is —C(O)N($R^3$)—, —C(S)N($R^3$)—, —C(O)CH($R^{21}$)—, —C(O)(O), or —C(O)—$L^2$—, wherein
      $R^{21}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —$OR^{23}$, —$SR^{23}$, —NH$_2$, —N(H)C(=NH)NH$_2$, —$COOR^{23}$, or —C(O)N($R^{23}$)$_2$; and
      $R^{23}$ is —H, $C_1$-$C_6$alkyl, or $C_1$-$C_6$ alkyl-aryl;
    $L^2$ is —$C_1$-$C_{24}$ alkyl- or -phenyl-$C_1$-$C_{24}$ alkyl-, wherein
      each alkyl group is optionally substituted with 1 to 4 groups which are oxo, =S, or —COOH; and
      one to six of the methylene groups in each alkyl group is optionally replaced by —O—, —S—, or —N($R^3$)—, provided that no two adjacent methylene groups are both replaced by —O—, —S—, or —N($R^3$)—; and
    $R^8$ is —H, —NH$_2$, or —OH; and Q is —O—, —S—, —N($R^3$)—, —N($R^3$)O—, —ON($R^3$)—, —CH$_2$—, or =NO—.

In a preferred embodiment of the first aspect, the invention provides the compound of formula (III),

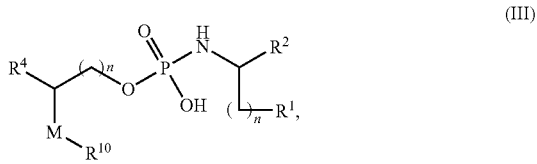

(III)

and pharmaceutically acceptable salts thereof, wherein each variable is as defined for formula (II).

In a preferred embodiment of the first aspect, the invention provides the compound of formula (IV),

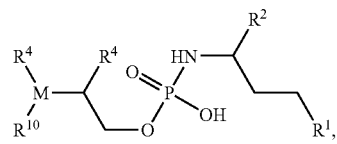

(IV)

and pharmaceutically acceptable salts thereof, wherein each variable is as defined for formula (II).

In a preferred embodiment of formulas (II)-(IV), $R^1$ and $R^2$ are each —C(O)OH.

In a preferred embodiment of formulas (II)-(IV), $R^4$ is —C(O)OH.

In a more preferred embodiment of formulas (II)-(IV), $R^1$, $R^2$, and $R^4$ are each —C(O)OH.

In a preferred embodiment of formulas (II)-(IV), $R^{10}$ is —C(O)-phenyl.

In a more preferred embodiment of formulas (II)-(IV), $R^{10}$ is $R^7$.

In a more preferred embodiment of formulas (II)-(IV), $R^{10}$ is $R^7$, wherein
  $R^7$ is —$L^1$—$R^8$, wherein
    $L^1$ is —C(O)—$L^2$—, wherein
      $L^2$ is —$C_1$-$C_{24}$ alkyl- or -phenyl-$C_1$-$C_{24}$ alkyl-, wherein
        each alkyl group is optionally substituted with 1 to 4 groups which are oxo, =S, or —COOH; and
        one to six of the methylene groups in each alkyl group is optionally replaced by —O—, —S—, or —N($R^3$)—, provided that no two adjacent methylene groups are both replaced by —O—, —S—, or —N($R^3$)—; and
    $R^8$ is —H, —NH$_2$, or —OH.

In a more preferred embodiment of formulas (II)-(IV), $R^{10}$ is $R^7$, wherein
  $R^7$ is —$L^1$—$R^8$, wherein
    $L^1$ is —C(O)—$L^2$—, wherein
      $L^2$ is —$C_1$-$C_{24}$ alkyl- or -phenyl-$C_1$-$C_{24}$ alkyl-, wherein
        each alkyl group is optionally substituted with 1 to 4 groups which are oxo or —COOH; and
        one to six of the methylene groups in each alkyl group is optionally replaced by —O—, or —N($R^3$)—, provided that no two adjacent methylene groups are both replaced by —O— or —N($R^3$)—; and
    $R^8$ is —H, —NH$_2$, or —OH.

In a more preferred embodiment of formulas (II)-(IV), $R^{10}$ is a peptide, dendrimer, or peptide dendrimer.

In a more preferred embodiment of the first aspect, the invention provides the compound according to formula (I) which is

| Compound | Name | Structure |
|---|---|---|
| T33 | N-{[(2S)-2-(benzoylamino)-2-carboxyethoxy](hydroxy)phosphoryl}-L-glutamic acid | 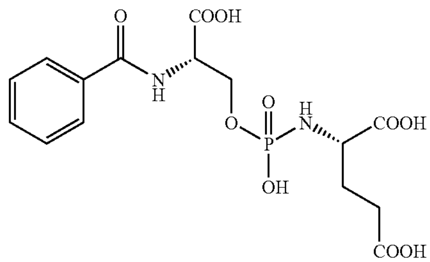 |
| L36 | N-[{(2S)-2-[benzoyl(methyl)amino]-2-carboxyethoxy}(hydroxy)phosphoryl]-L-glutamic acid | 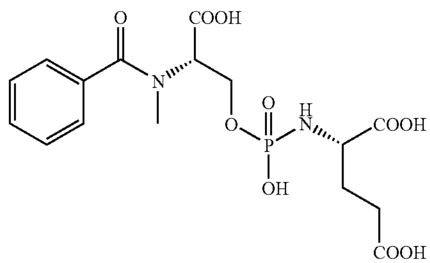 |
| TC5074 | N-{[2-(benzoylamino)ethoxy](hydroxy)phosphoryl}-L-glutamic acid | 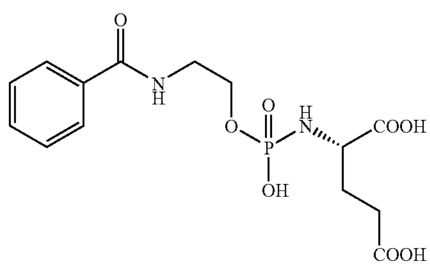 |
| L101 | N-[{2-[benzoyl(methyl)amino]ethoxy}(hydroxy)phosphoryl]-L-glutamic acid | 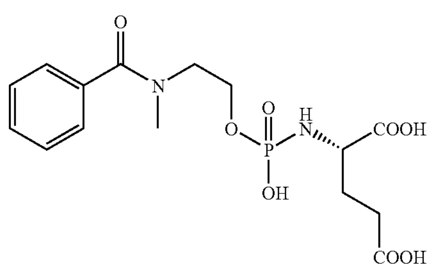 |
| NC-2-29 | N-[(biphenyl-4-ylmethoxy)(hydroxy)phosphoryl]-L-glutamic acid | 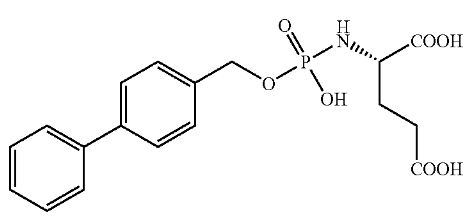 |
| MP1E | N-[(2-carboxy-4-phenylbutoxy)(hydroxy)phosphoryl]-L-glutamic acid | 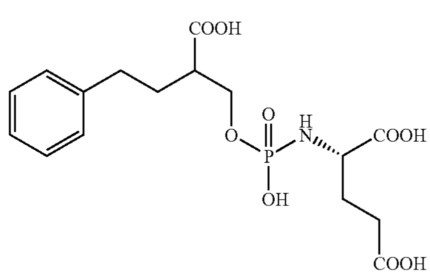 |

-continued
| Compound | Name | Structure |
|---|---|---|
| MP1D | N-[hydroxy(4-phenylbutoxy)phosphoryl]-L-glutamic acid | 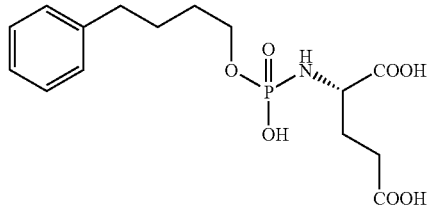 |
| LW-5-40 | N-{[(2S)-2-{[4-(aminomethyl)benzoyl]amino}-2-carboxy ethoxy](hydroxy)phosphoryl}-L-glutamic acid | 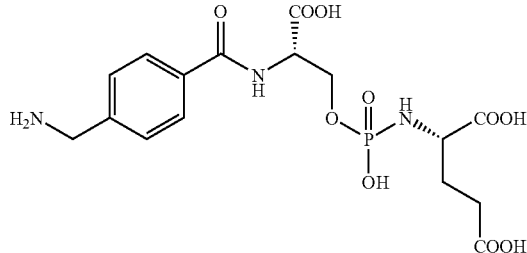 |
| LW-54 | L-γglutamyl-O-[{[(1S)-1,3-dicarboxy propyl]amino}(hydroxy)phosphoryl]-L-serine | 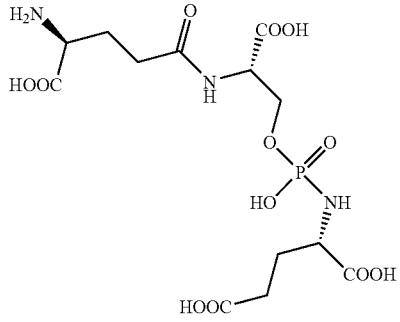 |
| LW-5-40 | N-{[(2S)-2-amino-2-carboxy ethoxy](hydroxy)phosphoryl}-L-glutamic acid | 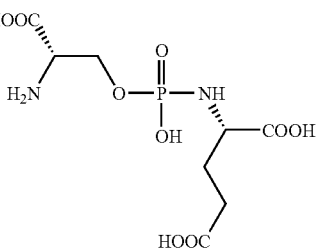 |

| Compound | Name | Structure |
|---|---|---|
| LW-II-108 | N-[{[(2S)-20-amino-2-carboxy-4,8-dioxo-6,12,15,18-tetraoxa-3,9-diazaicos-1-yl]oxy}(hydroxy)phosphoryl]-L-glutamic acid | 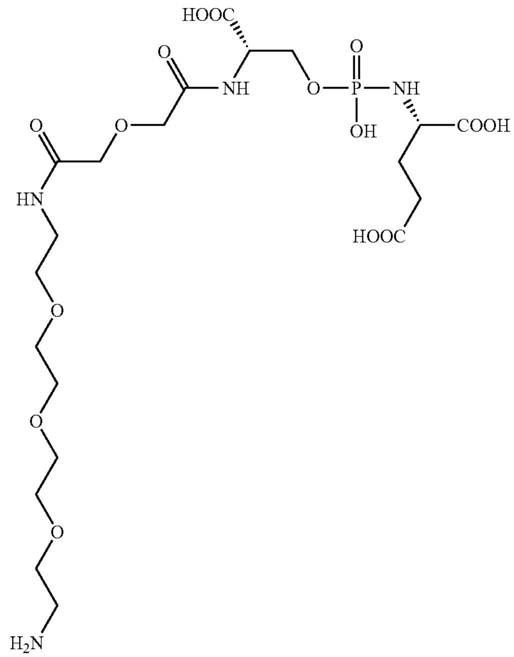 |

In a second aspect, the invention comprises chimeric compounds comprising a compound according to the first aspect of the invention covalently linked to a detectable label, therapeutic agent, or biomolecular anchor linked to a solid support. Examples of solid supports include commercially available polylysine-, maleic anhydride-, or streptavidin-coated 96-well plates. Other solid supports include commercially available gold-coated sensor chips or functionalized gold-coated sensor chips.

In one embodiment the detectable label is a fluorescent label. Standard fluorescent labels include Alexa Fluor dyes, BODIPY dyes, fluorescein-based dyes, rhodamine-based dyes, coumarin-based dyes, and pyrene-based dyes.

In another embodiment, the detectable label is one half of a specific binding pair, e.g., biotin of the biotin-streptavidin binding pair. Representative binding pair agents and biomolecular anchors include biotin, oligonucleotides of DNA or RNA, or lipids.

In another embodiment, the detectable label is a chelating structure able to bind radioisotopes such as $^{99}$Tc or MRI contrast agents such as Gd. Standard chelating agents include DOTA, DTPA, CHX-A", PCTA, and DO3A.

Standard fluorescent labels, binding pair agents, and chelating agents, and biomolecular anchors as described herein, may be used. Standard method known to those skilled in the art may be employed to link the compounds of the invention to such agents and anchors as well as to therapeutic agents.

The therapeutic agents are preferably compounds that interfere with one or more biological processes of cells that present PSMA and, therefore, treat or inhibit a disease associated with the PMSA-presenting cell. The therapeutic agents may optionally include chelated or covalently linked cytotoxic radioisotopes such as $^{90}$Y or $^{188}$Re, such chelating or covalent linking can be by means known to those of ordinary skill in the art.

Therapeutic agents include those that increase the immunogenicity of tumor cells either through direct attachment to the cell surface of cancer cells or through modulating the expression of antigenic peptides on cancer cells. Agents selected for covalent attachment will possess known anti-cancer, anti-proliferative, or cytotoxic properties. Alternatively, such agents will possess known properties that promote or increase the immunogenicity of cells as a target for T-cell immunosurveillance.

Therapeutic agents also include but are not limited to steroid-based agents such as 2-Methoxyestradiol, mifepristone, tamoxifen, inducers of apoptosis such as retinoic acid, histone deacetylase inhibitors such as butyrate, apoptosis inducing or cytotoxic siRNA such as Plk1 siRNA, antimitotic agents such as doxorubicin, antimetabolites such as methotrexate, and nanoparticles or liposomes designed to encapsulate a cytotoxic drug.

In an embodiment of the second aspect, the invention provides a compound of the formula, A—L—B, wherein
 A is glutamate or a glutamate analog;
 L is a phosphoramidate or a phosphoramidate analog;
 B is serine or a serine analog, and pharmaceutically acceptable salts thereof, wherein
 the compound is covalently bonded through a divalent linker to a detectable label, therapeutic agent, or biomolecular anchor linked to a solid support at any substitutable position of the compound.

In an embodiment of the second aspect, the divalent linker is derived from an amino acid, oligopeptide, poly(ethylene) glycol, oligoethylene glycol, and the like.

In an embodiment of the second aspect, the compound is covalently bonded to a detectable label.

In another embodiment of the second aspect, the compound is covalently bonded to a therapeutic agent.

In another embodiment of the second aspect, the compound is covalently bonded to a biomolecular anchor linked to a solid support.

In a preferred embodiment of the second aspect, the compound is covalently bonded to a detectable label, wherein the detectable label is a fluorescent label.

In another preferred embodiment of the second aspect, the compound is covalently bonded to a detectable label, wherein the detectable label is a chelating structure bound to a radioisotope or magnetic resonance imaging contrast agent.

In another preferred embodiment of the second aspect, the invention provides the compound of formula (VI),

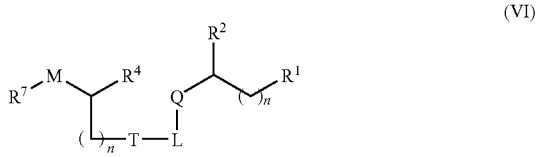
(VI)

and pharmaceutically acceptable salts thereof, wherein each n is independently 1, 2, 3, 4, 5 or 6;

each $R^1$ and $R^2$ are independently —C(O)$OR^3$, —C(O)N($R^3$)$_2$, —P(O)(O$R^3$)$_2$, —OP(O)(O$R^3$)$_2$, —S(O)$_2R^3$, —S(O)$_2OR^3$, —S(O)$_2$N($R^3$)$_2$, or tetrazolyl;

each $R^3$ is independently —H or $C_1$-$C_6$ alkyl;

$R^4$ is —H, —C(O)$OR^3$, —C(O)N($R^3$)$_2$, —P(O)(O$R^3$)$_2$, —OP(O)(O$R^3$)$_2$, —S(O)$_2R^3$, —S(O)$_2OR^3$, —S(O)$_2$N($R^3$)$_2$, or tetrazolyl;

L is —P(O)(O$R^3$)—, P(O)(N($R^3$)$_2$)—, —S(O)$_2$—, —C(O)—, or —C(S)—;

M and T are independently —O—, —S—, —N($R^3$)—, or —CH$_2$—;

$R^7$ is —X—$R^8$ or —$L^1$—$R^8$, wherein
 X is —C(O)—, —S(O)$_2$, —O—, —S—, or —N($R^3$)—;
 $L^1$ is —C(O)N($R^3$)—, —C(S)N($R^3$)—, —C(O)CH($R^{21}$)—, —C(O)(O), —C(O)—$L^2$—, a peptide, dendrimer, or peptide dendrimer, wherein
  $R^{21}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —O$R^{23}$, —S$R^{23}$, —NH$_2$, —N(H)C(=NH)NH$_2$, —COO$R^{23}$, or —C(O)N($R^{23}$)$_2$; and
  $R^{23}$ is —H, $C_1$-$C_6$ alkyl, or $C_1$-$C_6$ alkyl-aryl;
 $L^2$ is —$C_1$-$C_{24}$ alkyl- or -phenyl-$C_1$-$C_{24}$ alkyl-, wherein
  each alkyl group is optionally substituted with 1 to 4 groups which are oxo, =S, or —COOH; and
  one to six of the methylene groups in each alkyl group is optionally replaced by —O—, —S—, or —N($R^3$)—, provided that no two adjacent methylene groups are both replaced by —O—, —S—, or —N($R^3$)—; and
 $R^8$ is a therapeutic agent, detectable label, or biomolecular anchor linked to a solid support; and Q is —O—, —S—, —N($R^3$)O—, —ON($R^3$)—, —CH$_2$—, or =NO—.

In a preferred embodiment of the second aspect, the invention provides the compound of formula (VII),

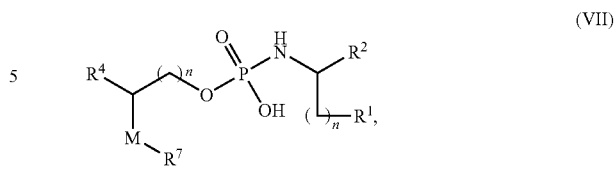
(VII)

and pharmaceutically acceptable salts thereof, wherein each variable is as defined for formula (VI).

In a preferred embodiment of the second aspect, the invention provides the compound of formula (VIII),

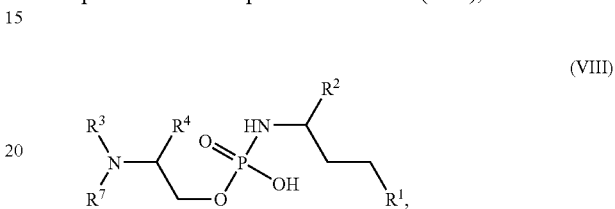
(VIII)

and pharmaceutically acceptable salts thereof, wherein each variable is as defined for formula (VI).

In a preferred embodiment of formulas (VI)-(VIII), $R^1$ and $R^2$ are each —C(O)OH.

In a preferred embodiment of formulas (VI)-(VIII), $R^4$ is —C(O)OH.

In a more preferred embodiment of formulas (VI)-(VIII), $R^1$, $R^2$, and $R^4$ are each —C(O)OH.

In a more preferred embodiment of formulas (VI)-(VIII), $L^1$ is —C(O)—$L^2$—, wherein
 $L^2$ is —$C_1$-$C_{24}$ alkyl- or -phenyl-$C_1$-$C_{24}$ alkyl-, wherein
  each alkyl group is optionally substituted with 1 to 4 groups which are oxo, =S, or —COOH; and
  one to six of the methylene groups in each alkyl group is optionally replaced by —O—, —S—, or —N($R^3$)—, provided that no two adjacent methylene groups are both replaced by —O—, —S—, or —N($R^3$)—.

In a more preferred embodiment of formulas (VI)-(VIII), $L^1$ is —C(O)—$L^2$—, wherein
 $L^2$ is —$C_1$-$C_{24}$ alkyl- or -phenyl-$C_1$-$C_{24}$ alkyl-, wherein
  each alkyl group is optionally substituted with 1 to 4 groups which are oxo or —COOH; and
  one to six of the methylene groups in each alkyl group is optionally replaced by —O— or —N($R^3$)—, provided that no two adjacent methylene groups are both replaced by —O— or —N($R^3$)—.

In a more preferred embodiment of formulas (VI)-(VIII), $L^1$ is a peptide, dendrimer, or peptide dendrimer.

In a preferred embodiment of formulas (VI)-(VIII), $R^8$ is a detectable label.

In a preferred embodiment of formulas (VI)-(VIII), $R^8$ is a biomolecular anchor linked to a solid support.

In a preferred embodiment of formulas (VI)-(VIII), $R^8$ is a detectable label, wherein the label is a fluorescent dye.

In a preferred embodiment of formulas (VI)-(VIII), $R^8$ is a detectable label, wherein the label is a fluorescent dye, wherein the fluorescent dye is Alexa Fluor, BODIPY, fluoresceins, rhodamine, coumarin, or pyrene-based dye.

In a preferred embodiment of formulas (VI)-(VIII), $R^8$ is a detectable label, wherein the label is a fluorescent dye, wherein the fluorescent dye is a fluorescein or fluorescein derivative.

In a preferred embodiment of formulas (VI)-(VIII), $R^8$ is a detectable label, wherein the label is a chelating agent.

In a preferred embodiment of formulas (VI)-(VIII), $R^8$ is a detectable label, wherein the label is a chelating agent, wherein the chelating agent is DOTA, DTPA, CHX-A", PCTA, and DO3A.

In a more preferred embodiment of formulas (VI)-(VIII), $R^8$ is $R^9$, wherein
$R^9$ is $C_1$-$C_6$ alkyl, aryl, or $C_1$-$C_6$ alkyl-aryl, wherein $R^9$ is substituted with one to three groups which are independently —COOH or $N(R^{91})_2$, wherein
each $R^{91}$ is independently —H or $C_1$-$C_6$ alkyl substituted with 1 to 3 groups which are independently —COOH or —$N(R^{92})_2$ wherein
each $R^{92}$ is independently —H or $C_1$-$C_6$ alkyl substituted with 1 to 3 COOH.

In a preferred embodiment of formulas (VI)-(VIII), $R^8$ is a detectable label, wherein the label is one half of a specific binding pair.

In a preferred embodiment of formulas (VI)-(VIII), $R^8$ is a detectable label, wherein the label is one half of a specific binding pair, wherein the one half of the specific binding pair is biotin, an oligonucleotide of DNA or RNA, or a lipid.

In a preferred embodiment of formulas (VI)-(VIII), $R^8$ is a detectable label, wherein the label is one half of a specific binding pair, wherein the one half of the specific binding pair is biotin.

In a preferred embodiment of formulas (VI)-(VIII), $R^8$ is a therapeutic agent.

In a more preferred embodiment of formulas (VI)-(VIII), $R^8$ is a steroidal group optionally substituted with 1 to 5 groups selected from the group consisting of $C_1$-$C_{10}$ alkyl, oxo, hydroxy, or halogen.

In another preferred embodiment of the first aspect, the invention provides the compound of formula (IX),

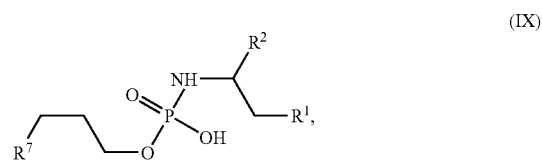

(IX)

and pharmaceutically acceptable salts thereof, wherein
$R^7$ is —O—$R^8$, wherein $R^8$ is a steroidal group optionally substituted with 1 to 5 groups selected from the group consisting of $C_1$-$C_{10}$ alkyl, oxo, hydroxy, or halogen; and each remaining variable is as defined for formula (VI).

In a more preferred embodiment of the first aspect, the invention provides the compounds according to formula (VI) which is

| Compound | Name | Structure |
|---|---|---|
| LW-39-F5EX | N-{[(2S)-2-carboxy-2-({4-[({3-[(2-{[3-carboxy-4-(6-hydroxy-3-oxo-9,9a-dihydro-3H-xanthen-9-yl)phenyl]amino}-2-oxoethyl)thio]propanoyl}amino)methyl]benzoyl}amino)ethoxy](hydroxy)phosphoryl}-L-glutamic acid | 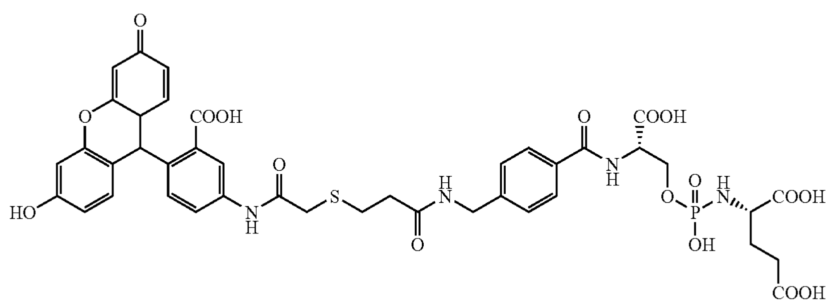 |
| LW-39-5FAMX | N-[{(2S)-2-carboxy-2-[(4-{[(6-{[3-carboxy-4-(6-hydroxy-3-oxo-9,9a-dihydro-3H-xanthen-9-yl)benzoyl]amino}hexanoyl)amino]methyl}benzoyl)amino]ethoxy}(hydroxy)phosphoryl]-L-glutamic acid | 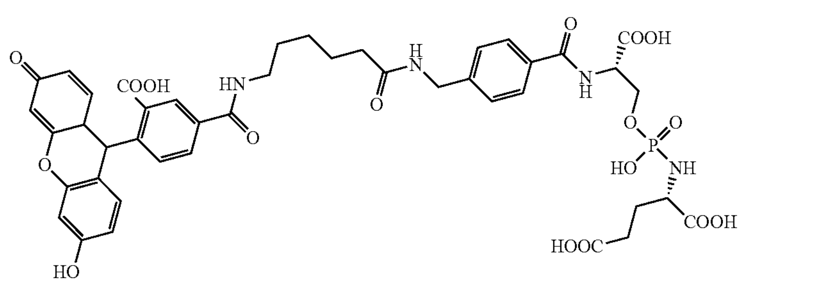 |

-continued

| Compound | Name | Structure |
|---|---|---|
| LW-54-F5EX | N-{3-[(2-{[3-carboxy-4-(6-hydroxy-3-oxo-9,9a-di hydro-3H-xanthen-9-yl) phenyl]amino}-2-oxoethyl) thio]propanoyl}-L-γ-glutamyl -O-[{[(1S)-1,3-dicarboxy propyl]amino}(hydroxy) phosphoryl]-L-serine | 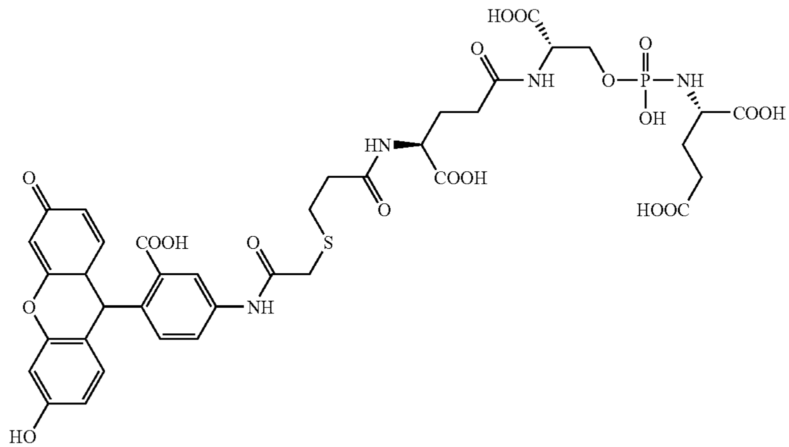 |
| LW-54-5FAMX | N-(6-{[3-carboxy-4-(6-hydroxy-3-oxo-9,9a-di hydro-3H-xanthen-9-yl) benzoyl]amino}hexanoyl)-L-γ -glutamyl-O-[{[(1S)-1,3-dicarboxypropyl]amino} (hydroxy)phosphoryl]-L-serine | 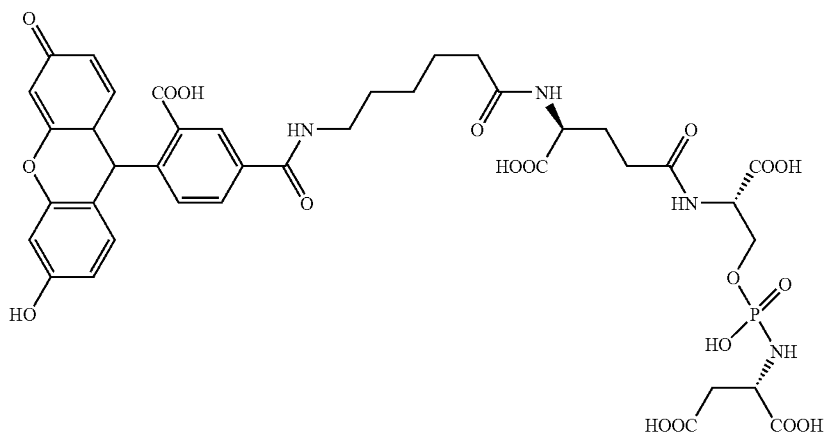 |
| L6-VI-21 | N-[{(2S)-2-carboxy-2-[({[3-carboxy-4-(6-hydroxy-3-oxo-9,9a-dihydro-3H-xanthen-9-yl)phenyl]amino} carbonothioyl)amino]ethoxy} (hydroxy)phosphoryl]-L-glutamic acid | 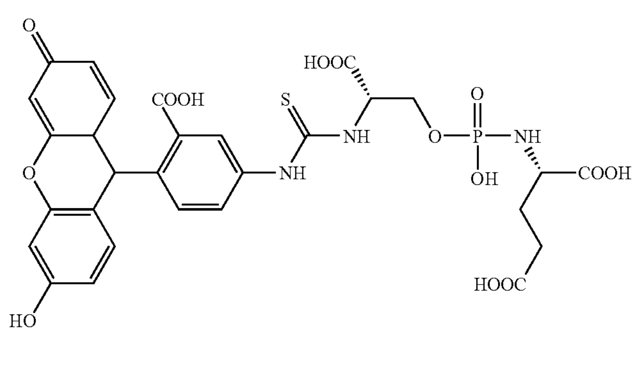 |

-continued

| Compound | Name | Structure |
|---|---|---|
| TL-LW-54-BnDTPA | N-{[(4-{2-[bis(carboxy methyl)amino]-3-[{2-[bis (carboxymethyl)amino]ethyl} (carboxymethyl)amino] propyl}phenyl)amino] carbonothioyl}-L-γ-glutamyl-O-[{[(1S)-1,3-dicarboxy propyl]amino}(hydroxy)phos phoryl]-L-serine | 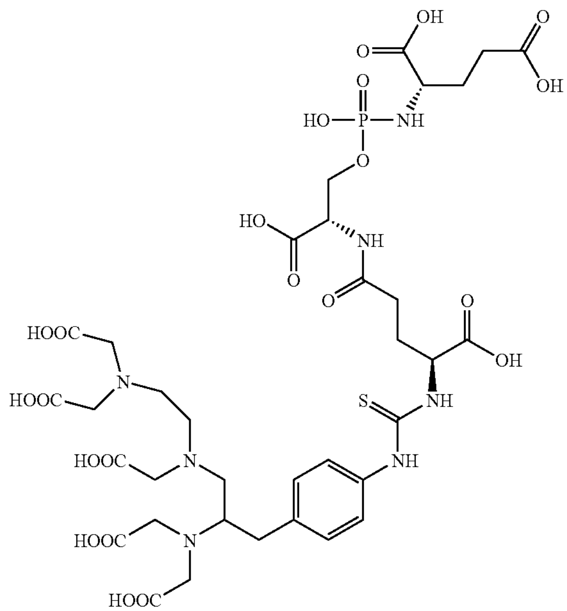 |
| TL-LW-54-LC-LC-Biotin | N-{6-[(6-{[5-(2-oxohexa hydro-1H-thieno[3,4-d]imi dazol-4-yl)pentanoyl]amino} hexanoyl)amino]hexanoyl} -L-γ-glutamyl-O-[{[(1S)-1,3-dicarboxypropyl]amino}(hy droxy)phosphoryl]-L-serine | 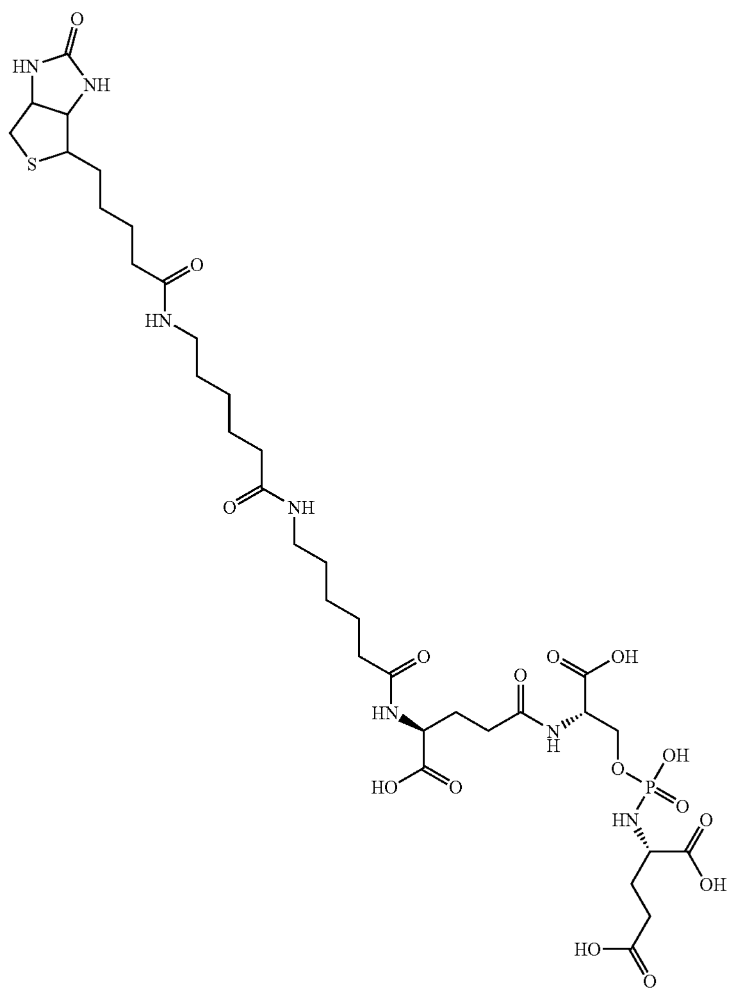 |

-continued

| Compound | Name | Structure |
|---|---|---|
| TL-LW-39-LC-LC-Biotin | N-{[(2S)-2-carboxy-2-({4-[({6-[(6-{[5-(2-oxohexahydro-1H-thieno[3,4-d]imidazol-4-yl)pentanoyl]amino}hexanoyl)amino]hexanoyl}amino)methyl]benzoyl}amino)ethoxy](hydroxy)phosphoryl}-L-glutamic acid | 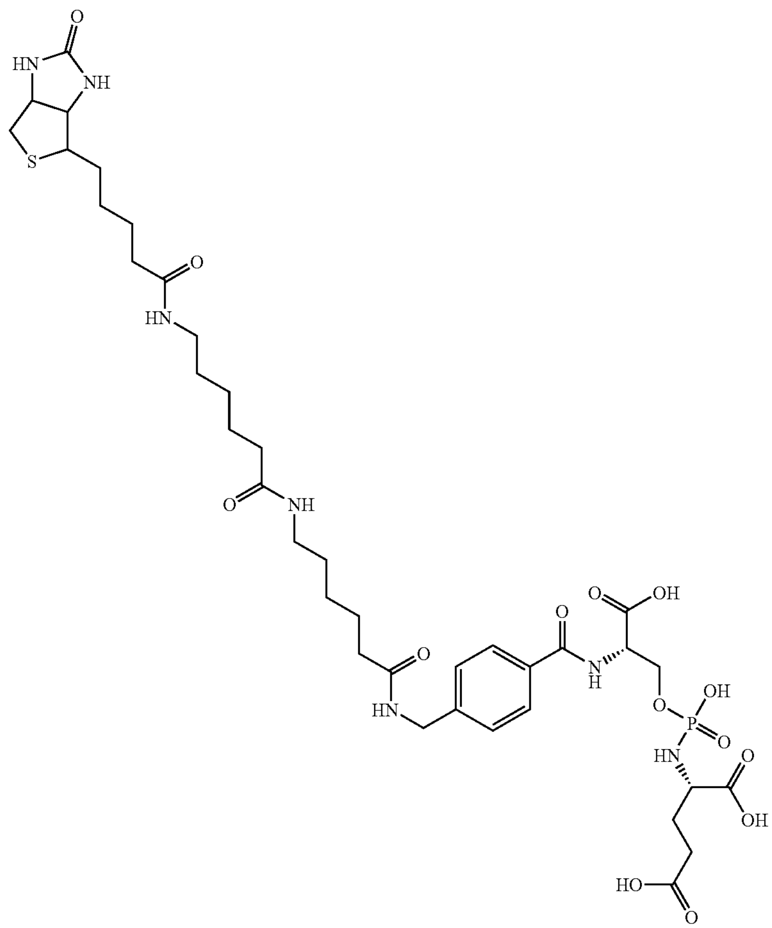 |
| LW-S-120A1 | N-[{3-[(3 β,8ξ,9ξ,14ξ,17ξ,20ξ)-cholestan-3-yloxy]propoxy}(hydroxy)phosphoryl]-L-glutamic acid | 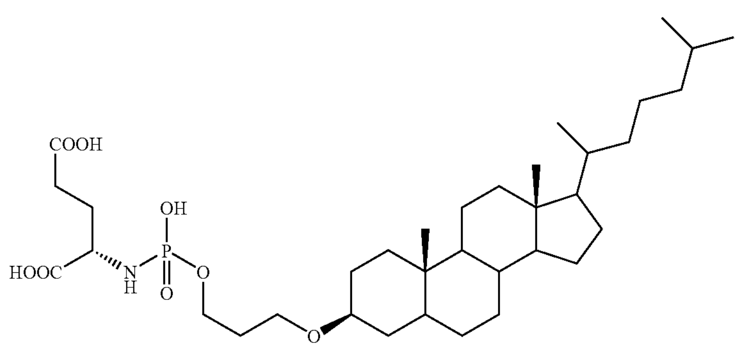 |
| LW-S-120A3 | N-[hydroxy(3-{[(3β,8ξ,9ξ,14ξ)-17-oxoandrostan-3-yl]oxy}propoxy)phosphoryl]-L-glutamic acid | 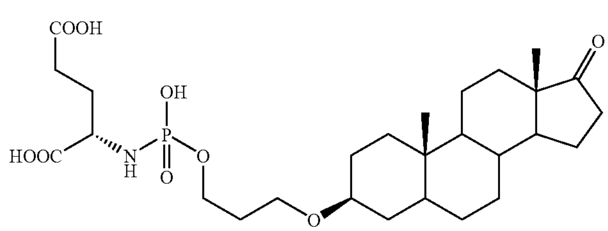 |

-continued

| Compound | Name | Structure |
|---|---|---|
| LW-A-149 | N-{[(3β,8ξ,9ξ,14ξ,17ξ,20ξ)-cholestan-3-yloxy](hydroxy)phosphoryl}-L-glutamic acid | 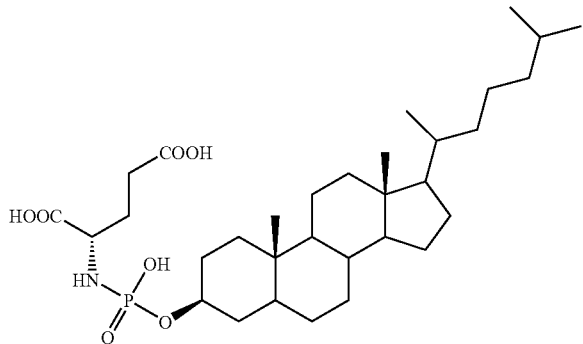 |
| LW-S-120A2 | N-(hydroxy{[(3β,8ξ,9ξ,14ξ)-17-oxoandrostan-3-yl]oxy}phosphoryl)-L-glutamic acid | 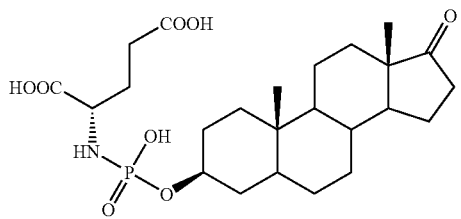 |
| LW-A-152 | N-[hydroxy(3-{[17-oxoestra-1(10),2,4-trien-3-yl]oxy}propoxy)phosphoryl]-L-glutamic acid | 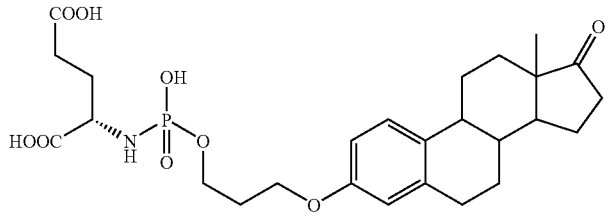 |
| LW-A-151 | N-[(3-{[3-(benzoyloxy)estra-1(10),2,4-trien-17-yl]oxy}propoxy)(hydroxy)phosphoryl]-L-glutamic acid | 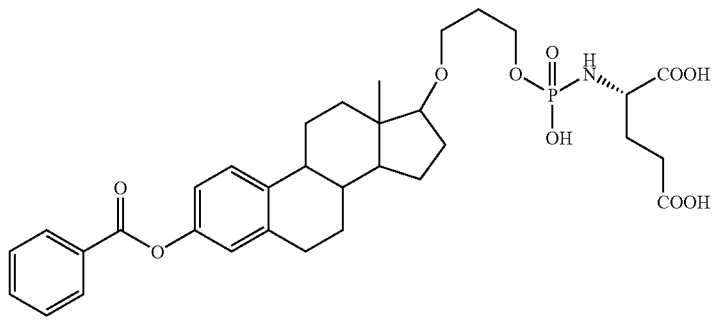 | and pharmaceutically acceptable salts thereof.

In a third aspect, the invention comprises a composition comprising a chimeric compound according to the second aspect of the invention, or pharmaceutically acceptable salt thereof, and a pharmaceutically acceptable carrier, diluent, or excipient.

In a fourth aspect, the invention comprises a diagnostic kit comprising a chimeric compound according to the second aspect of the invention. In one embodiment according to this aspect of the convention, the detectable label or biomolecular anchor is one member of a specific binding pair (e.g., biotin) and the kit comprises the other member of the specific binding pair.

In a fifth aspect, the invention comprises a method of detecting PMSA-presenting cells, the method comprising contacting cells suspected of presenting PMSA with a chimeric compound according to the second aspect of the invention and measuring for the presence of the detectable label under conditions in which the detectable label is detected only when bound to a PMSA-presenting cell. How the detectable label is detected will, of course, depend upon the label being used and will be clear to those skilled in the art. For example, if the detectable label is a near-infrared fluorescent label, detecting the label can be accomplished with in vivo fluorescence imaging.

In a sixth aspect, the invention comprises a method of inhibiting or treating a disease involving cells presenting PMSA comprising contacting the cells or causing the cells to be contacted with a compound according to the second aspect of the invention or a composition according to the third aspect of the invention wherein the chimeric compound comprises a compound according to the first aspect of the invention covalently linked to a therapeutic agent. In one embodiment of this aspect, the invention comprises administering the composition to a mammalian subject (preferably human) that has a disease involving PMSA-presenting cells in an amount effective to inhibit or treat the disease. Appropriate formulations and methods of administration can be routinely determined using standard methods.

In a seventh aspect, the invention comprises a method for capturing, detecting, and quantifying PMSA-presenting cells, the method comprising contacting cells suspected of presenting PMSA with a chimeric compound according to the second aspect of the invention and detecting captured or immobilized PSMA-presenting cells. In a preferred embodiment of the seventh aspect, the chimeric compound of the second aspect is linked to a biomolecular anchor on a solid support. How the cells are detected will, of course, depend upon the sensing device being used and will be clear to those skilled in the art. For example, if the chimeric compound according to the second aspect of the invention is linked to solid support, detection of PSMA-presenting cells can be accomplished directly using plasmon resonance or can be accomplished once cells are released and labeled with a fluorescent label using flow cytometry.

Representative dendrimers which may be used in the invention are described in J. M. J. Fréchet, D. A. Tomalia, *Dendrimers and Other Dendritic Polymers*, John Wiley & Sons, Ltd. NY, N.Y. (2002).

Representative compounds useful in the combination of the present invention include those compounds described above, and their pharmaceutically acceptable acid and base addition salts and solvates thereof. If the compound of the invention is obtained as an acid addition salt, the free base can be obtained by basifying a solution of the acid salt. Conversely, if the product is free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

Non-toxic pharmaceutical salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

The compounds of the invention and/or compositions thereof find particular use in the inhibition and/or treatment of PMSA-related diseases in animals and humans. Accordingly, another aspect of the invention is administration of a therapeutically effective amount of one or more compounds of the invention or compositions containing the one or more compounds of the invention to a patient in need of such treatment for PMSA-related diseases. Preferably the patient is a mammal, most preferably a human. When used in this context, the compounds may be administered per se, but are typically formulated and administered in the form of a pharmaceutical composition. The exact composition will depend upon, among other things, the method of administration and will apparent to those of skill in the art. A wide variety of suitable pharmaceutical compositions are described, for example, in *Remington's Pharmaceutical Sciences*, 20$^{th}$ ed., 2001).

Formulations suitable for oral administration can consist of (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5-100 mg/ml compound and about 1000 mg/ml propylene glycol in water. Another specific example of a suitable solution formulation may comprise from about 0.5-100 mg/ml compound and from about 800-1000 mg/ml polyethylene glycol 400 (PEG 400) in water.

A specific example of a suitable suspension formulation may include from about 0.5-30 mg/ml compound and one or more excipients selected from the group consisting of: about 200 mg/ml ethanol, about 1000 mg/ml vegetable oil (e.g., corn oil), about 600-1000 mg/ml fruit juice (e.g., grapefruit juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml compound, about 100-200 mg/ml lecithin (or other phospholipid or mixture of phospholipids) and optionally about 5 mg/ml cholesterol in water. For subcutaneous administration of compound 9, a liposome suspension formulation including 5 mg/ml compound in water with 100 mg/ml lecithin and 5 mg/ml compound in water with 100 mg/ml lecithin and 5 mg/ml cholesterol provides good results. This formulation may be used for other compounds of the invention.

The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents, discussed in more detail, below.

In another aspect, the invention comprises a method of making a composition for the treatment and/or inhibition of a PMSA-related disease, the method comprising admixing a compound of the invention with a pharmaceutically acceptable carrier, diluent, and/or excipient.

In therapeutic use for the treatment of PMSA-related diseases, the compounds utilized in the pharmaceutical method of the invention are administered to patients diagnosed with PMSA-related diseases at dosage levels suitable to achieve therapeutic benefit. By therapeutic benefit is meant that the administration of compound leads to a beneficial effect in the patient over time. Therapeutic benefit is also achieved if the administration of compound slows or halts altogether the adverse symptoms which typically accompany PMSA-related diseases.

The compounds of the invention and/or compositions thereof may also be administered prophylactically in patients who are at risk of developing PMSA-related diseases.

Initial dosages suitable for administration to humans may be determined from in vitro assays or animal models. For example, an initial dosage may be formulated to achieve a serum concentration that includes the $IC_{50}$ of the particular compound being administered, as measured in an in vitro assay. Alternatively, an initial dosage for humans may be based upon dosages found to be effective in animal models of PMSA-related diseases. Exemplary suitable model systems are described, for example, in Muchmore, 2001, Immunol. Rev. 183:86-93 and Lanford & Bigger, 2002, Virology, 293: 1-9, and the referenced cited therein. As one example, the initial dosage may be in the range of about 0.01 mg/kg/day to about 200 mg/kg/day, or about 0.1 mg/kg/day to about 100 mg/kg/day, or about 1 mg/kg/day to about 50 mg/kg/day, or about 10 mg/kg/day to about 50 mg/kg/day, can also be used. The dosages, however, may be varied depending upon the requirements of the patient, the severity of the condition being treated, and the compound being employed. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

DEFINITIONS

All compounds here were named using ACD/Name 8.00 (Product Release 8.17, Build: 4 May 2005; http://www.acd-labs.com; Toronto, ON, Canada)

Compounds of the present invention can exist as stereoisomers, wherein asymmetric or chiral centers are present. The present invention contemplates various stereoisomers and mixtures thereof and are specifically included within the scope of this invention. Stereoisomers include enantiomers, diastereomers, and mixtures of enantiomers or diastereomers.

The term "alkyl" as used herein, means a straight or branched chain hydrocarbon containing from 1 to 24 carbon atoms unless otherwise defined. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkyl-aryl" as used herein, means an aryl group, as defined herein bonded to the parent moiety via an alkyl group, as defined herein. Examples of alkyl-aryl groups include, but are not limited to benzyl and phenethyl.

The term "alkyl-heteroaryl" as used herein, means a heteroaryl group, as defined herein bonded to the parent moiety via an alkyl group, as defined herein. Examples of alkyl-heteroaryl groups include, but are not limited to pyridylmethyl and 2-pyridylethyl.

The term "aryl," as used herein, means phenyl or a bicyclic aryl or a tricyclic aryl. The bicyclic aryl is naphthyl, or a phenyl fused to a cycloalkyl, or a phenyl fused to a cycloalkenyl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, azulenyl, dihydroanthracenyl, fluorenyl, and tetrahydrophenanthrenyl.

The term "heteroaryl," as used herein, means a monocyclic heteroaryl or a bicyclic heteroaryl. The monocyclic heteroaryl is a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, indazolyl, indolyl, isoquinolinyl, naphthyridinyl, quinolinyl, tetrahydroquinolinyl, and thienopyridinyl.

The term "halo" or "halogen" as used herein, means —Cl, —Br, —I or —F.

The term "hydroxy" as used herein, means an —OH group.

The term "methylene" as used herein, means a —CH$_2$— group.

The term "oxo" as used herein, means a =O moiety.

The term "peptide" as used herein means a peptide with two to ten amino acid residues.

The term "steroidal" as used herein means a monoradical of a group with the general tetracyclic structure,

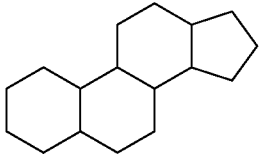

wherein the tetracyclic structure may be fully saturated or contain 1 or more unsaturated bonds and may be bonded to the parent moiety at any available substitutable position. For example, one or more of the cyclic subunits may be aromatic.

The term "glutamate analog" as used herein means a chemical structure intended to mimic the structure of glutamic acid. Such a structure chemical structure would be designed around the molecular framework of glutamic acid which consists of an amino group or a bioisostere of an amino group and two carboxylic acids or bioisosteres of carboxylic acids similarly positioned relative to one another as in the structure of glutamic acid. For example, the amino group could be replaced with a thiol, hydroxyl, hydroxylamino, oxime, or methylene group. One or both of the carboxylic acids could be replaced with a carboxamide, phosphonate, phosphate, sulfonate or tetrazole group. A glutamate analog would also consist of both cyclic and acyclic chemical structures as well as homologous (shorter or longer) structures. Examples of such glutamate analogs that are biologically active and can be used in the present invention have been recently reviewed. *Aspartate and glutamate mimetic structures in biologically active compounds.* (Stefanic P, Dolenc M S. *Curr Med Chem.* 2004 April; 11(8):945-68), which is hereby incorporated by reference in its entirety.

The term "serine analog" as used herein means a chemical structure intended to mimic the structure of serine. Such a structure would be designed around the molecular framework of serine which consists of an amino group or a bioisostere of an amino group, a carboxylic acid or bioisostere of carboxylic acid, and a hydroxyl group or bioisostere of a hydroxyl group similarly positioned relative to one another as in the structure of serine itself. For example, the amino group could be replaced with a thiol, hydroxyl, or methylene group. The carboxylic acids could be replaced with a carboxamide, phosphonate, phosphate, sulfonate or tetrazole group. The carboxylic acid could be removed altogether. The hydroxyl group could be replaced with an amino, thiol, or methylene group. A serine analog would also consist of both cyclic and acyclic chemical structures as well as homologous (shorter or longer) structures.

The term "phosphoramidate analog" as used herein means a chemical structure that would mimic the molecular structure of a phosphoramidate with zinc-binding capability. For example, a phosphoramidate analog could be a phosphonamidate, phosphonate, phosphate, phosphinate, sulfonamide, urea, N-hydroxyurea, thiourea, carbamate, hydroxamate, reverse hydroxamate, N-hydroxyamide, or N-hydroxycarbamate group.

The term "a fluorescein" refers to compounds of the general formula,

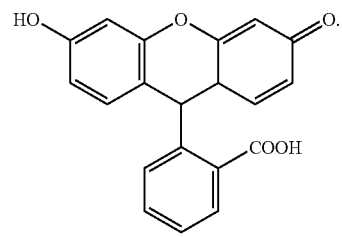

The term "fluorescein derivative" refers a fluorescein as defined herein which is optionally substituted with one to three groups which are independently halogen or alkyl, each as defined herein.

EXAMPLES

Scheme 1 presents a representative synthetic scheme for the synthesis of phosphoramidate inhibitor T33. Using this general strategy, over 15 analogs of phosphoramidate T33 of varying complexity have been synthesized. This scheme, in conjunction with standard synthetic methodologies, can be used to prepare compounds according to the first aspect of the invention. Compounds according to the second aspect of the invention can be routinely prepared therefrom using standard synthetic methodologies.

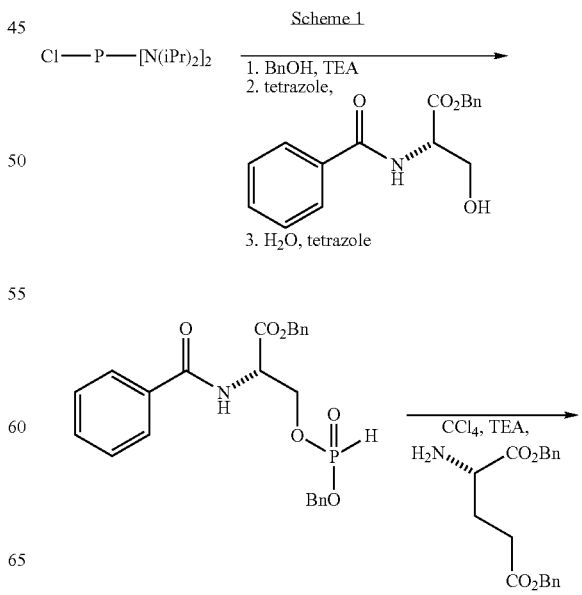

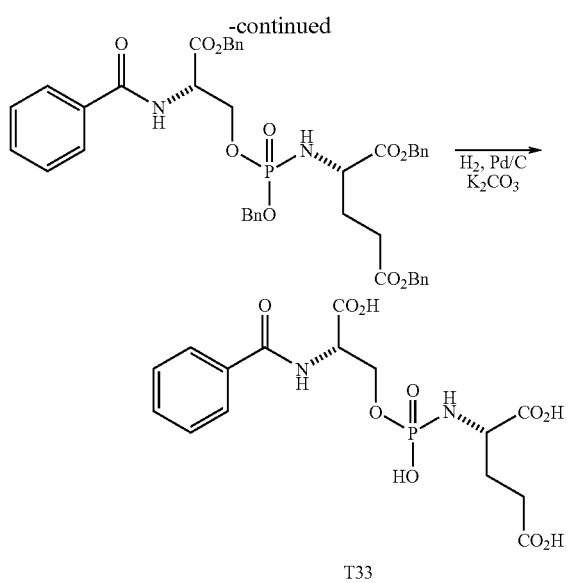

T33

Example 1

PMSA Inhibition Assay

Adapted from, Maung, J.; Mallari, J. P.; Girtsman, T. A.; Wu, L. Y.; Rowley, J. A.; Santiago, N. M.; Brunelle, A.; Berkman, C. E. Probing for a Hydrophobic a Binding Register in Prostate-Specific Membrane Antigen with Phenylalkylphosphonamidates. Bioorg. Med. Chem. 2004, 12, 4969.

Working solutions of the substrate (N-[4-(phenylazo)benzoyl]-glutamyl-g-glutamic acid, PAB-Glu-γ-Glu) and all inhibitors were made in TRIS buffer (50 mM, pH 7.4). Working solutions of purified PSMA were appropriately diluted in TRIS buffer (50 mM, pH 7.4) to provide from 15% to 20% conversion of substrate to product in the absence of inhibitor. A typical incubation mixture (final volume 250 µL) was prepared by the addition of either 25 µL of an inhibitor solution or 25 µL TRIS buffer (50 mM, pH 7.4) to 175 µL TRIS buffer (50 mM, pH 7.4) in a test tube. A volume of the 25 µL PAB-Glu-γ-Glu (100 µM) was added to the above solution. The enzymatic reaction was initiated by the addition of 25 µL of the PSMA working solution. In all cases, the final concentration of PAB-Glu-γ-Glu was 10 µM while the enzyme was incubated with five serially-diluted inhibitor concentrations to provide a range of inhibition from 10% to 90% inhibition. The reaction was allowed to proceed for 15 min with constant shaking at 37° C. and was terminated by the addition of 25 µL methanolic TFA (2% trifluoroacetic acid by volume in methanol) followed by vortexing. The quenched incubation mixture was quickly buffered by the addition of 25 µL $K_2HPO_4$ (0.1 M), vortexed, and centrifuged (10 min at 7000 g). An 85 µL aliquot of the resulting supernatant was subsequently quantified by HPLC. $IC_{50}$ values were calculated using Kaleida-Graph 3.6 (Synergy Software).

PABGγG and its hydrolytic product (PABG) were separated and quantified using an analytical reversed-phase HPLC column (Lichrosphere C18 5 µm, 150×4.6 mm; Phenomenex, Torrence, Calif.) with a mobile phase consisting of ACN/potassium phosphate [25 mM, pH 2.0 (adjusted with $H_3PO_4$)] at a respective volume ratio of 40:60. At a flow rate of 1.0 ml/min, PABGγG and its hydrolytic product (PABG) were detected at 325 nm with retention times of 4.8 and 6.9 min, respectively.

Example 2

Identification of Potent Inhibitors of PSMA Through the Molecular Pruning of Phosphoramidate Analogs of Gamma-Diglutamate We designed and synthesized the phosphoramidate T33 as a lead compound for the inhibition of PSMA. Its design was based upon the structures of known PSMA substrates such as gamma-glutamate derivatives of folate analogs. Initial screening of T33 indicated that it displayed considerable potency against PSMA ($IC_{50}$<50 nM). To better understand the importance of various structural elements of T33 for inhibitory potency against PSMA, we conducted a molecular pruning study in which we created a library of T33 analogs as shown in FIG. 1. The synthesis of the three compounds from this library were previously reported in the literature: CCS, JM139 (Lu, H.; Ng, R.; Shieh, C. C.; Martinez, A. R.; Berkman, C. E. Inhibition of Glutamate Carboxypeptidase by Phosphoryl and Thiophosphoryl Derivatives of Glutamic and 2-Hydroxyglutaric Acid. *Phosphorus, Sulfur and Silicon*, 2003, 178, 17), and 2-PMPA (Jackson, P. F.; Cole, D. C.; Slusher, B. S.; Stetz, S. L.; Ross, L. E.; Donzanti, B. A.; Trainor, D. A. Design, synthesis, and biological activity of a patent inhibitor of the neuropeptidase N-acetylated-linked acidic dipeptidase. J. Med. Chem. 1996, 39, 619-622.) The remaining compounds in FIG. 1, FIG. 2, and FIGS. 7-12 are novel compounds of the invention.

All compounds in the library described in FIG. 1, FIG. 2, and FIGS. 7-12 were screened for inhibitory potency of PSMA using the assay described in Example 1.

Screening of the library in FIG. 1 against purified PSMA from LNCaP cells by our published method (Purification of Prostate-Specific Membrane Antigen with Conformational Epitope-Specific Antibody-Affinity Chromatography. Liu, T.; Toriyabe, Y.; Berkman, C. E. *Prot. Exp. Purif.* 2006, 49, 251) indicated that two general structures displayed superior inhibitory potency: intact phosphoramidate peptidomimetics such as T33 and L36 as well as simple P1' analogs such as CCS, JM140, and 2-PMPA.

Figure 2:
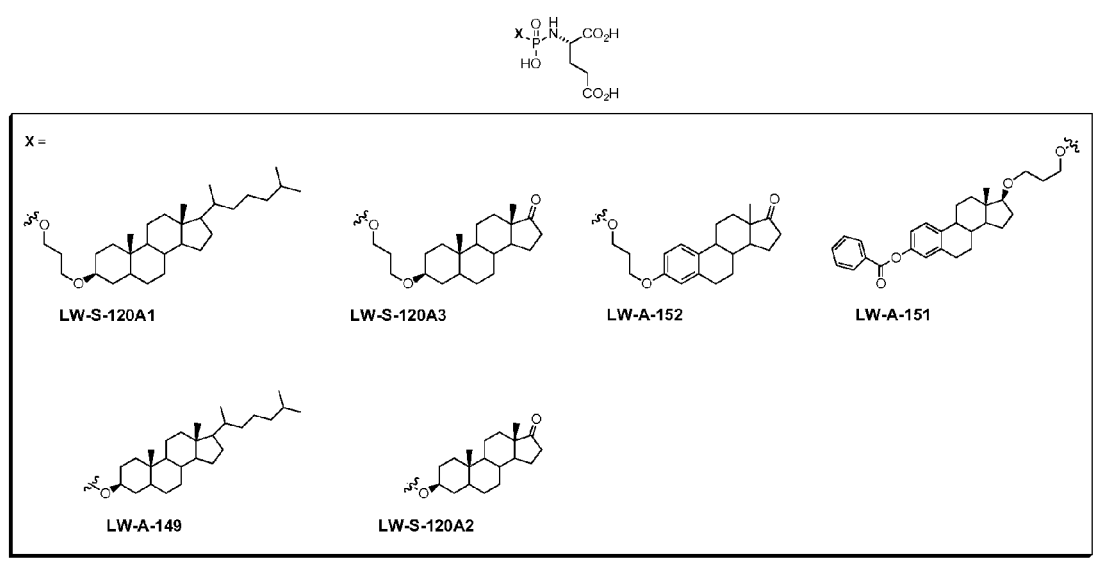
FIG. 2 displays steroid-containing phosphoramidate inhibitors of PSMA.

Despite the lack of additional affinity elements, it is hypothesized that the dibasic phosphoryl motif of CCS, JM140, and 2-PMPA is responsible for their enhanced affinity for PSMA through strong interactions with PSMA's active-site zinc atoms. Interestingly, considerable affinity is maintained in the simple hydrophobic analog MP1D. The ability of PSMA to accommodate hydrophobic and spatially demanding ligand was further confirmed when we prepared and screened a library of steroid-containing phosphoramidate inhibitors (FIG. 2). All compounds in FIG. 2 manifested an $IC_{50}$ of less than 1 µM as determined by the assay described in Example 1. The inhibition assay results from MP1D and the steroid-containing phosphoramidate inhibitors are in agreement with our previous work in which we identified the existence of a hydrophobic binding domain remote from the central catalytic machinery of PSMA (Maung, J.; Mallari, J. P.; Girtsman, T. A.; Wu, L. Y.; Rowley, J. A.; Santiago, N. M.; Brunelle, A.; Berkman, C. E. Probing for a Hydrophobic a Binding Register in Prostate-Specific Membrane Antigen with Phenylalkylphosphonamidates. *Bioorg. Med. Chem.* 2004, 12, 4969).

Example 3

Time-Dependent and Irreversible Inhibition of PSMA by T33 Analogs

Figure 3:
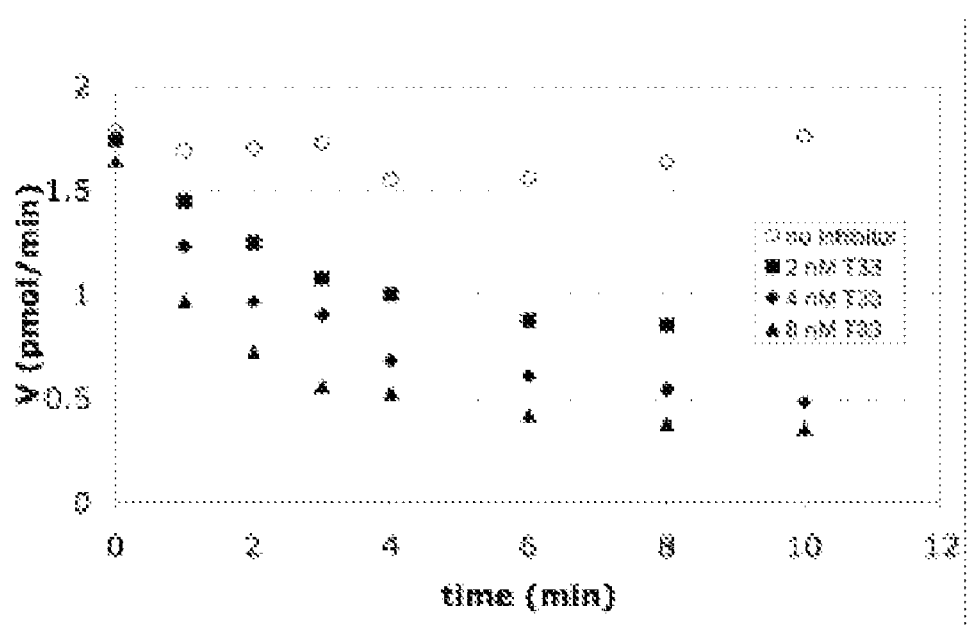
FIG. 3 displays time-dependent PSMA inhibition by T33
Figure 4:
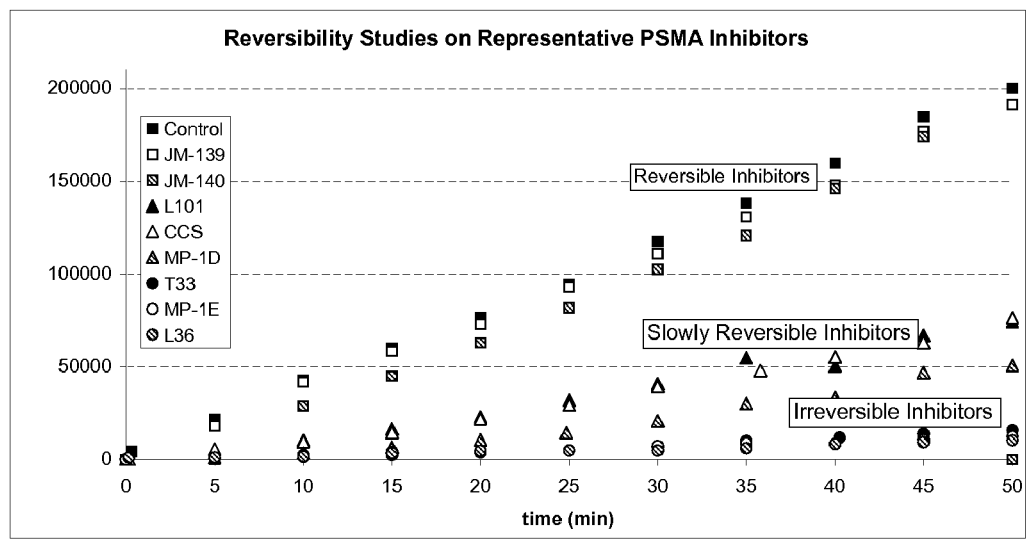
FIG. 4 displays the irreversible and slowly-reversible inhibition of T33 and representative molecular pruning analogs.
Figure 5:
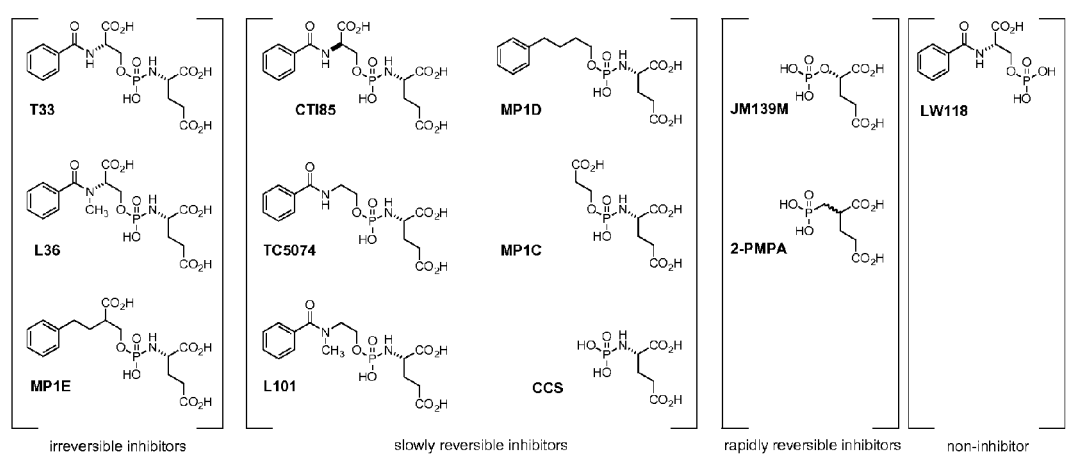
FIG. 5 displays a categorization of T33 and its molecular pruning analogs as irreversible, slowly reversible, and rapidly reversible inhibitors of PSMA.

Surprisingly, we found that the PSMA-inhibitory compounds in the T33 analog library (FIG. 1) were not only potent inhibitors of PSMA but exhibited a time-dependent loss of enzymatic activity as shown in FIG. 3. This unique result has led us to hypothesize that T33 and its analogs are unique slow binding inhibitors. In some cases, the inhibition appears to be irreversible. Such is the case for T33, L36, and MP1E as PSMA activity cannot be recovered by 100-fold dilution of the enzyme inhibited by these compounds (FIG. 4). These results strongly suggest that T33, L36, and MP1E are either mechanism-based irreversible inhibitors of PSMA or they are functionally irreversible inhibitors of PSMA potentially leading to dramatic conformational changes and potentially causing covalent damage to the enzyme. In addition to T33, L36, and MP1E, we have recently demonstrated that LW-54 and LW-39 are also irreversible inhibitors of PSMA. Based upon a survey of the literature, this is the first discovery of time-dependent and irreversible inhibitors of PSMA. While slow binding inhibition of zinc peptidases and proteases by phosphorus acid derivatives is a known phenomenon, mechanism-based irreversible inhibitors for such enzymes are rare. The inhibitors from FIG. 1 are categorized as irreversible and slowly-reversible inhibitors in FIG. 5. All compounds displayed in FIG. 5 manifested in $IC_{50}$ of less than 1 μM.

Example 4

Inhibitor Induced Homodimer Formation

Figure 6:
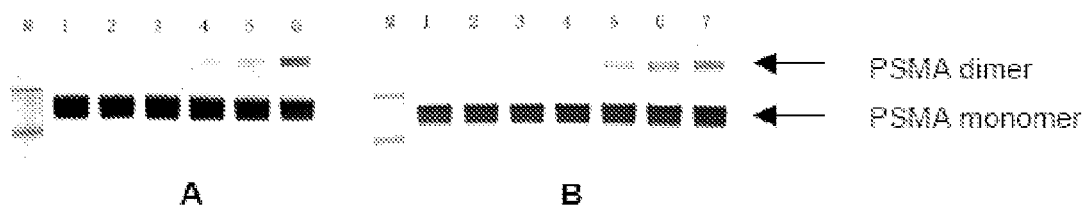
FIG. 6 displays Western blots of PSMA treated with T33 over (A) increasing time and (B) increasing concentration.
Figure 7:
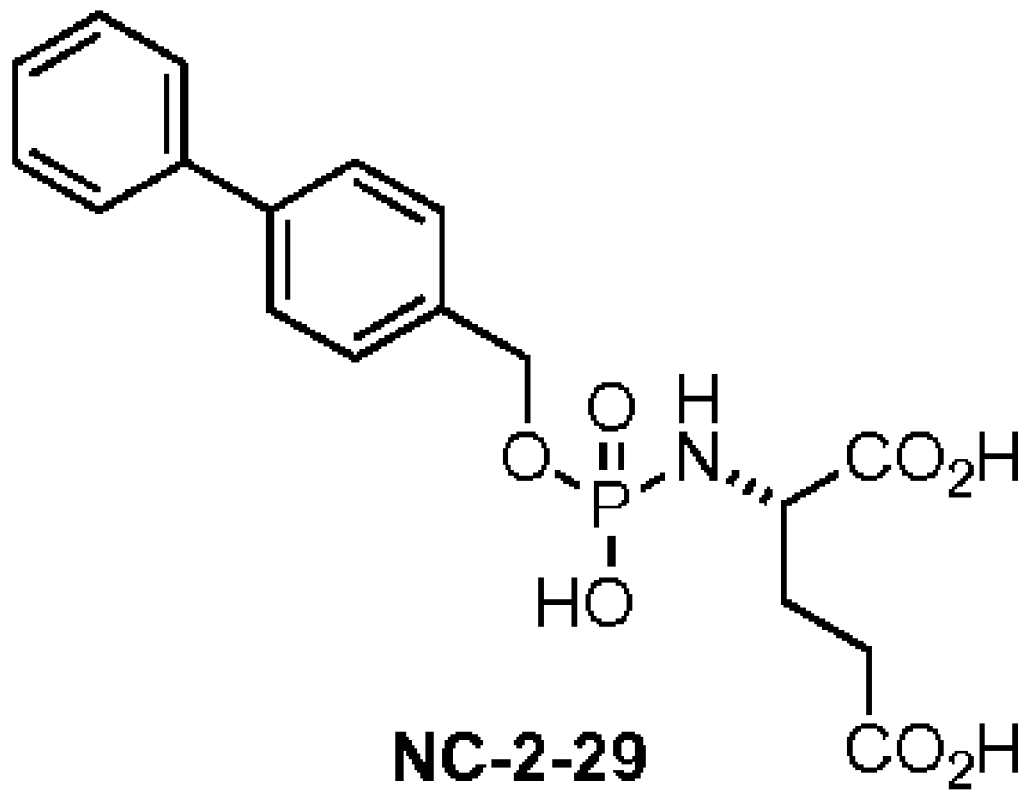
FIG. 7 displays a biphenyl analog of MP1D.

With regard to the action of phosphoramidates T33 and L36, we have demonstrated that treatment of PSMA with these inhibitors result in the formation of covalent PSMA homodimers as indicated by Western blots. As shown in the representative example in FIG. 6, covalent PSMA dimer formation mediated by T33 is both concentration dependent and time-dependent. These results coincide with the time-dependent enzymatic inhibition of PSMA by phosphoramidate T33 and its analogs as described above. More importantly, these data are in agreement with the irreversible inhibition profiles of compounds T33, L36, and MP1D. These data suggest that T33 and L36 are involved in covalent modifications of PSMA promoting inter-protein crosslinking and potentially intra-protein crosslinking. Although we have not determined the mechanism of inhibition for T33, L36 and MP1D, it is clear that these agents represent a unique class of inhibitors of PSMA that may be used as covalent delivery vehicles specific for PSMA-expressing cancer cells. Based upon a cursory literature review, this is the first design and preparation of irreversible covalent modifiers of PSMA.

Example 5

Specificity of Phosphoramidate Inhibitors for PSMA

To determine that the design of the phosphoramidate inhibitors of the invention is specific to PSMA, a preliminary study was conducted with representative compounds from the T33 analog library (FIG. 1) with matrix metalloproteinase-9 (MMP-9). The MMP enzymes are zinc-dependent endopeptidases involved in the degradation of extracellular matrices. Of the series of compounds examined including NC-2-29, only one compound (NC-2-29) exhibited inhibitory potency against MMP-9 with a Ki value of 5 mM. T33 has been recently assayed for inhibition of MMP-2 and demonstrated no inhibition at concentrations up to 10 μM. These predominantly negative results suggest that the general structural framework of the T33-based inhibitors of the invention confer specificity for the target metallopeptidase, PSMA.

Example 6

Inhibitor-Directed Labeling of PSMA-Expressing Prostate Cancer Cells

Figure 8:
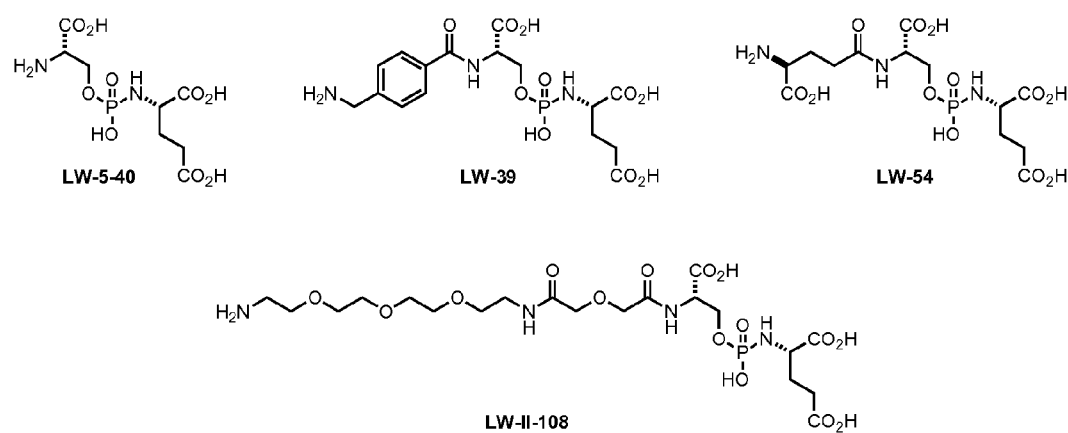
FIG. 8 displays synthetic PSMA inhibitors designed for both derivatization at the N-terminus amino group and for delivery of imaging and therapeutic payloads to prostate cancer cells.
Figure 9:
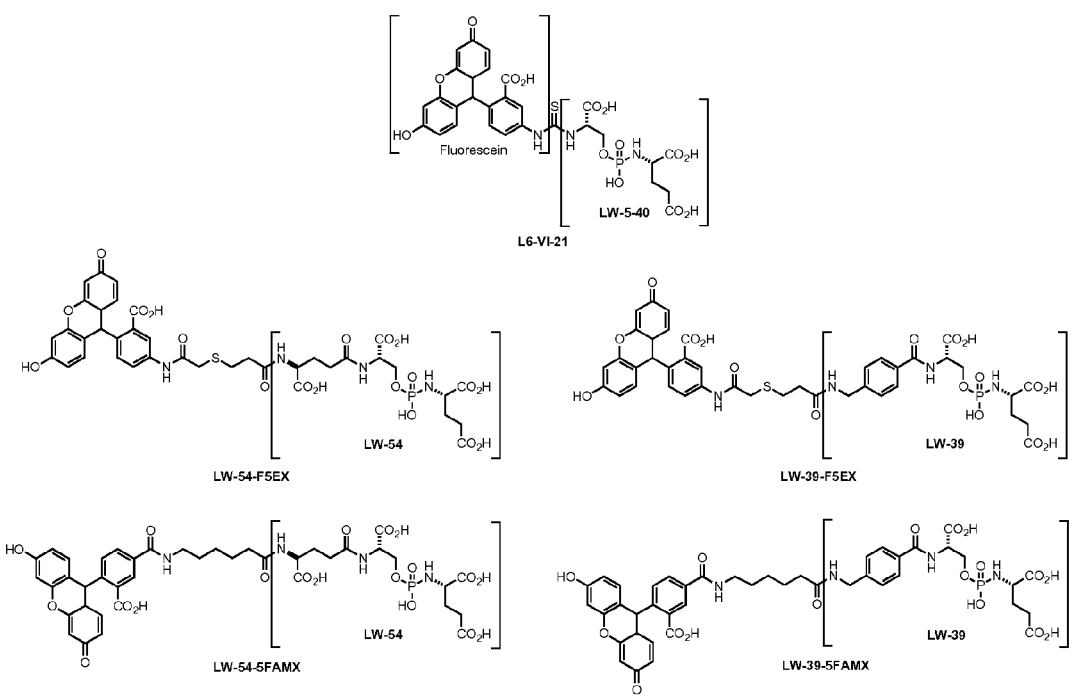
FIG. 9 displays fluorescently labeled PSMA inhibitors known to specifically label PSMA-expressing prostate cancer cells.
Figure 10:
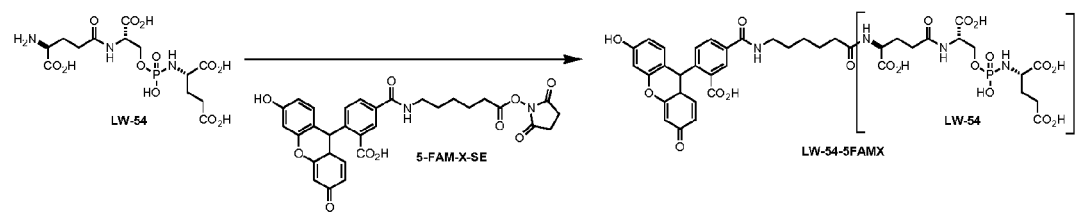
FIG. 10 displays a representative preparation for fluorescently-labeled PSMA inhibitors.
Figure 11:
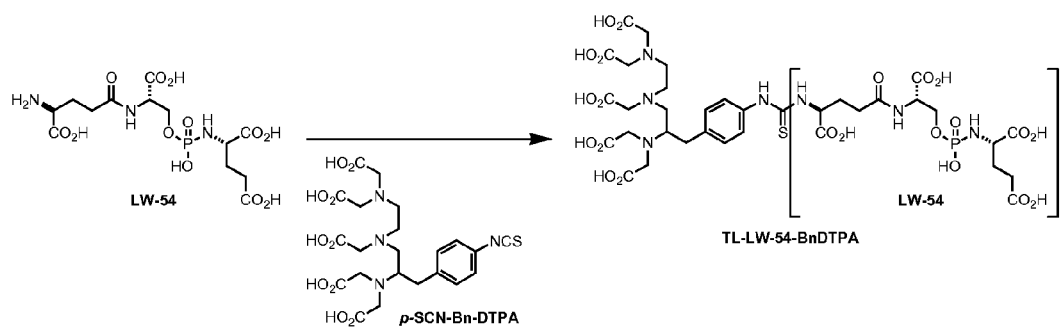
FIG. 11 displays the preparation of a chelator-bearing PSMA inhibitor TL-LW-54-BnDTPA.
Figure 12:
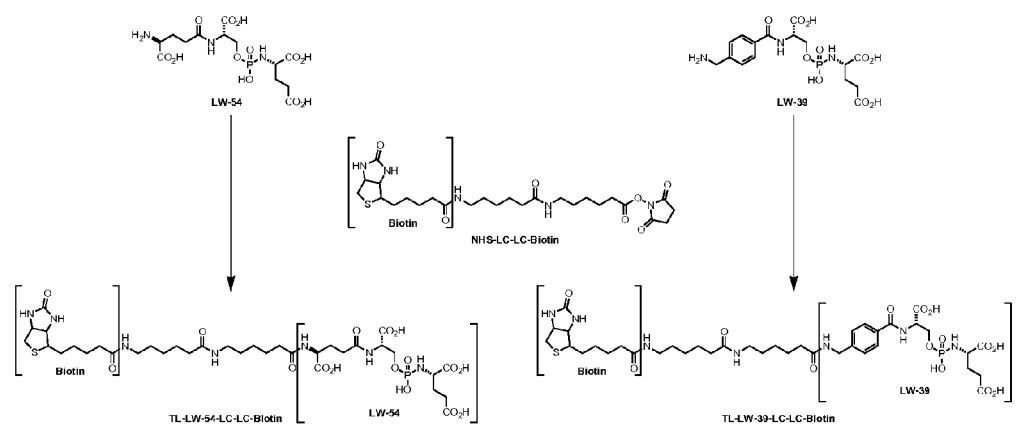
FIG. 12 displays representative biotin-labeled PSMA inhibitors.

Recent experiments have demonstrated that imaging payloads (such as organic fluorophores) can be specifically delivered to PSMA-expressing prostate cancer cells. We designed and synthesized four PSMA inhibitors that each possesses an N-terminus amino group as a point of attachment for imaging or therapeutic payloads (FIG. 8).

These compounds have been subsequently derivatized with amine-reactive fluorescent dyes (FIG. 9) to specifically label PSMA-expressing prostate cancer cells. Based upon fluorescence microscopy data, each of these compounds have been demonstrated to specifically label PSMA-expressing prostate cancer cells (LNCaP cells) and not label cells that do not express PSMA (PC3 cells). The thiourea-linked fluorescent inhibitor L6-V1-21 exhibited an $IC_{50}$ of 85 nM against PSMA. This result demonstrates that inhibitory potency was not abolished when the inhibitor core was derivatized with a structural motif of considerable size. PSMA-expressing prostate cancer cells (LNCaP) treated with L6-VI-21 resulted in specific labeling as observed by fluorescence microscopy. Confocal microscopy was conducted on both LNCaP and PC3 prostate cancer cells after treatment with L6-V1-21 and propidium iodide.

When LNCaP cells are treated with L6-V1-21, fluorescence microscopy confirms extensive cell-surface labeling by L6-V1-21 as shown by strong green fluorescent labeling of the cells. When LNCaP cells are treated with L6-V1-2 and propidium iodide, confocal fluorescence microscopy confirms extensive cell-surface labeling by L6-V1-21 as shown by strong green fluorescent labeling on the surface of the cells while red fluorescence was observed for the cell nuclei from propidium iodide staining. When PC3 cells are treated with L6-V1-2 and propidium iodide, confocal fluorescence microscopy confirms specificity of L6-V1-2 for PSMA-expressing cells (LNCaP) as no green fluorescent labeling on the surface of the cells is observed for PC3 cells but red fluorescence is observed for the cell nuclei from propidium iodide staining. The PC3 cells served as a negative control because they do not express PSMA. While propidium iodide stained the nuclei of both cell lines, only the surface of the PSMA-expressing LNCaP 6 cells were fluorescently labeled with L6-V1-21. The intensely labeled sites on these LNCaP cells are hypothesized to be locations in which PSMA has aggregated.

Fluorescence microscopy of LNCaP cells treated with the fluorescent inhibitor LW-54-F5EX demonstrated that small-molecule inhibitors of PSMA are substantially equivalent to an antibody (3C6) in delivering and labeling PSMA-expressing cells with a fluorescent dye. In that experiment, both LW-54 and the antibody 3C6 each labeled with fluorescein-5-EX specifically labeled the membranes of LNCaP cells. When LNCaP cells are treated with either LW-54-F5EX or the fluorescently labeled antibody 3C6-F5EX, fluorescence microscopy confirms extensive cell-surface labeling in both cases by as evidenced by strong green fluorescent labeling of the cell surfaces. To confirm that LW-54-F5EX was specific for PSMA-expressing cells, both LNCaP and PC3 cells were treated with this compound. While DAPI (4',6-diamidino-2-phenylindole) stained nuclear DNA in both cell lines, only LNCaP cells were fluorescently labeled with LW-54-F5EX. When LNCaP cells are treated with LW-54-F5EX and DAPI, fluorescence microscopy confirms extensive cell-surface labeling by LW-54-F5EX as shown by strong green fluorescent labeling on the surface of the cells while blue fluorescence is observed for the cell nuclei from DAPI staining. When PC3 cells are treated with LW-54-F5EX and DAPI, fluorescence microscopy confirms specificity of LW-54-F5EX for PSMA-expressing cells (LNCaP) as no green fluorescent labeling on the surface of the cells is observed for PC3 cells but blue fluorescence is observed for the cell nuclei from DAPI staining. Because PC3 cells do not express PSMA, these results confirm that small-molecule agents such as 54-F5EX are specific to PSMA-expressing cancer cells.

Fluorescence microscopy of LNCaP cells treated with the fluorescent inhibitor LW-54-5FAMX again demonstrated that small-molecule inhibitors of PSMA are substantially equivalent to antibodies in delivering and labeling PSMA-expressing cells with a fluorescent dye. In that experiment, both LNCaP and PC3 cells were treated with LW-54-5FAMX. While DAPI (4',6-diamidino-2-phenylindole) stained nuclear DNA in both cell lines, only LNCaP cells were fluorescently labeled with LW-54-5FAMX. When LNCaP cells are treated with LW-54-5FAMX and DAPI, fluorescence microscopy confirms extensive cell-surface labeling by LW-54-5FAMX as shown by strong green fluorescent labeling on the surface of the cells while blue fluorescence is observed for the cell nuclei from DAPI staining. When PC3 cells are treated with LW-54-5FAMX and DAPI, fluorescence microscopy confirms specificity of LW-54-5FAMX for PSMA-expressing cells (LNCaP) as no green fluorescent labeling on the surface of the cells is observed for PC3 cells but blue fluorescence is observed for the cell nuclei from DAPI staining. These results confirm that small-molecule agents such as LW-54-5FAMX are specific to PSMA-expressing cancer cells.

The above results from cell-labeling studies confirm that LNCaP-specific labeling can be achieve by small-molecule, non-biological inhibitors of PSMA. These results serve as a proof that small molecule inhibitors of PSMA can specifically deliver imaging or therapeutic payloads to PSMA-expressing cancer cells.

It is understood that the foregoing detailed description and accompanying Examples are merely illustrative and are not to be taken as limitations upon the scope of the invention, which is defined by the appended claims. Various changes and modifications to the disclosed embodiments will be apparent to those skilled in the art. Such changes and modifications, including without limitation those relating to the chemical structures, substituents, derivatives, intermediates, syntheses, and/or methods of use of the invention, may be made without departing from the spirit and scope thereof.

Each journal article, book, patent, and patent application referred to herein is hereby incorporated by reference in its entirety.

I claim:

1. The compound or pharmaceutically acceptable salt thereof, of the formula,

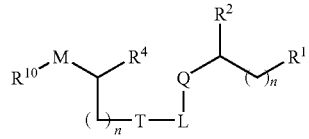

wherein
each n is independently 1, 2, 3, 4, 5 or 6;
each $R^1$ and $R^2$ are independently —C(O)O$R^3$, —C(O)N($R^3$)$_2$, —P(O)(O$R^3$)$_2$, —OP(O)(O$R^3$)$_2$, —S(O)$_2$$R^3$, —S(O)$_2$O$R^3$, —S(O)$_2$N($R^3$)$_2$, or tetrazolyl;
each $R^3$ is independently —H or $C_1$-$C_6$ alkyl;
$R^4$ is —H, —C(O)O$R^3$, —C(O)N($R^3$)$_2$, —P(O)(O$R^3$)$_2$, —OP(O)(O$R^3$)$_2$, —S(O)$_2$$R^3$, —S(O)$_2$O$R^3$, —S(O)$_2$N($R^3$)$_2$, or tetrazolyl;
L is —P(O)(O$R^3$)—, or —P(O)(N($R^3$)$_2$)—;
M and T are independently —O—, —S—, —N($R^3$)—, or —CH$_2$—;
$R^{10}$ is —H, —$C_1$-$C_6$ alkyl, aryl, —$C_1$-$C_6$ alkyl-aryl, -aryl-aryl, —X—$R^6$, —$R^7$, —C(O)$R^5$, —S(O)$_2$$R^5$, peptide, dendrimer, or peptide dendrimer, wherein
X is —O—, —S—, or —N($R^3$)—;
$R^5$ is —CH($R^{51}$)N($R^{52}$)$_2$; $C_1$-$C_6$ alkyl optionally substituted with 1 to 3 groups which are independently -halogen, COO$R^{53}$, or —N($R^{52}$)$_2$; aryl; or heteroaryl, wherein
$R^{51}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —O$R^{53}$, —S$R^{53}$, —NH$_2$, —N(H)C(=NH)NH$_2$, —COO$R^{53}$, or —C(O)N($R^{53}$)$_2$; and
$R^{52}$ is —H, $C_1$-$C_6$alkyl, —C(O)$R^{53}$, C(O)O$R^{53}$, —C(O)NH($C_1$-$C_6$alkyl), —C(O)N($R^{53}$)$_2$, —C(O)aryl, or —C(O)heteroaryl;
$R^{53}$ is —H, $C_1$-$C_6$alkyl, or $C_1$-$C_6$ alkyl-aryl;
$R^6$ is —H or $C_1$-$C_6$ alkyl;
and
$R^7$ is —$L^1$—$R^8$, wherein
$L^1$ is —C(O)N($R^3$)—, —C(S)N($R^3$)—, —C(O)CH($R^{21}$)—, —C(O)(O), or —C(O)—$L^2$—,
wherein
$R^{21}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —O$R^{23}$, —S$R^{23}$, —NH$_2$, —N(H)C(=NH)NH$_2$, —COO$R^{23}$, or —C(O)N($R^{23}$)$_2$; and
$R^{23}$ is —H, $C_1$-$C_6$alkyl, or $C_1$-$C_6$ alkyl-aryl;
$L^2$ is —$C_1$-$C_{24}$ alkyl- or -phenyl-$C_1$-$C_{24}$ alkyl-, wherein
each alkyl group is optionally substituted with 1 to 4 groups which are oxo, =S, or —COOH; and
one to six of the methylene groups in each alkyl group is optionally replaced by —O—, —S—, or —N($R^3$)—, provided that no two adjacent methylene groups are both replaced by —O—, —S—, or —N($R^3$)—; and
$R^8$ is —H, —NH$_2$, or —OH; and
Q is —O—, —S—, —N($R^3$)—, —N($R^3$)O—, —ON($R^3$)—, —CH$_2$—, or =NO—.

2. The compound or pharmaceutically acceptable salt thereof of claim 1 of the formula,

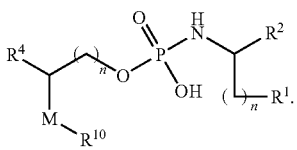

3. The compound or pharmaceutically acceptable salt thereof of claim 1 of the formula,

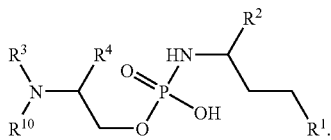

4. The compound or pharmaceutically acceptable salt thereof of claim 3, wherein each $R^1$ and $R^2$ is —C(O)OH.

5. The compound or pharmaceutically acceptable salt thereof of claim 3, wherein $R^{10}$ is —C(O)-phenyl.

6. The compound or pharmaceutically acceptable salt thereof of claim 3, wherein $R^{10}$ is $R^7$.

7. The compound of claim 1 which is

---

N-{[(2S)-2-(benzoylamino)-2-carboxyethoxy](hydroxy)phosphoryl}-L-glutamic acid;
N-[{(2S)-2-[benzoyl(methyl)amino]-2-carboxyethoxy}(hydroxy)-phosphoryl]-L-glutamic acid;
N-{[2-(benzoylamino)ethoxy](hydroxy)phosphoryl}-L-glutamic acid;
N-[{2-[benzoyl(methyl)amino]ethoxy}(hydroxy)phosphoryl]-L-glutamic acid;
N-[(biphenyl-4-ylmethoxy)(hydroxy)phosphoryl]-L-glutamic acid;
N-[(2-carboxy-4-phenylbutoxy)(hydroxy)phosphoryl]-L-glutamic acid;
N-[hydroxy(4-phenylbutoxy)phosphoryl]-L-glutamic acid;
N-{[(2S)-2-{[4-(aminomethyl)benzoyl]amino}-2-carboxyethoxy]-(hydroxy)phosphoryl}-L-glutamic acid;
L-γ-glutamyl-O-[{[(1S)-1,3-dicarboxypropyl]amino}(hydroxy)-phosphoryl]-L-serine;
N-{[(2S)-2-amino-2-carboxyethoxy](hydroxy)phosphoryl}-L-glutamic acid;
N-[{[(2S)-20-amino-2-carboxy-4,8-dioxo-6,12,15,18-tetraoxa-3,9-diazaicos-1-yl]oxy}(hydroxy)phosphoryl]-L-glutamic acid;
or a pharmaceutical acceptable salt thereof.

--- or a pharmaceutical acceptable salt thereof.

8. The compound or pharmaceutically acceptable salt thereof of the formula,

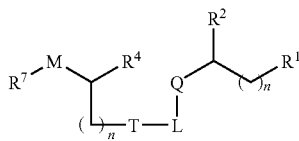

wherein
each n is independently 1, 2, 3, 4, 5 or 6;
each $R^1$ and $R^2$ are independently —C(O)$OR^3$, —C(O)N($R^3$)$_2$, —P(O)(O$R^3$)$_2$, —OP(O)(O$R^3$)$_2$, —S(O)$_2R^3$, —S(O)$_2$O$R^3$, —S(O)$_2$N($R^3$)$_2$, or tetrazolyl;
each $R^3$ is independently —H or $C_1$-$C_6$ alkyl;
$R^4$ is —H, —C(O)$OR^3$, —C(O)N($R^3$)$_2$, —P(O)(O$R^3$)$_2$, —OP(O)(O$R^3$)$_2$, —S(O)$_2R^3$, —S(O)$_2$O$R^3$, —S(O)$_2$N($R^3$)$_2$, or tetrazolyl;
L is —P(O)(O$R^3$)—, or —P(O)(N($R^3$)$_2$)—;
M and T are independently —O—, —S—, —N($R^3$)—, or —CH$_2$—;
$R^7$ is —X—$R^8$ or —$L^1$—$R^8$, wherein
X is —O—, —S—, or —N($R^3$)—;
$L^1$ is —C(O)N($R^3$)—, —C(S)N($R^3$)—, —C(O)CH($R^{21}$)—, —C(O)(O)—, —C(O)—$L^2$—, a peptide, dendrimer, or peptide dendrimer, wherein
$R^{21}$ is —H, aryl, heteroaryl, $C_1$-$C_6$ alkyl-aryl optionally substituted with —OH; $C_1$-$C_6$ alkyl-heteroaryl, or $C_1$-$C_6$ alkyl optionally substituted with —O$R^{23}$, —S$R^{23}$, —NH$_2$, —N(H)C(=NH)NH$_2$, —COO$R^{23}$, or —C(O)N($R^{23}$)$_2$; and
$R^{23}$ is —H, $C_1$-$C_6$alkyl, or $C_1$-$C_6$ alkyl-aryl;
$L^2$ is —$C_1$-$C_{24}$ alkyl- or -phenyl-$C_1$-$C_{24}$ alkyl-, wherein
each alkyl group is optionally substituted with 1 to 4 groups which are oxo, =S, or —COOH; and
one to six of the methylene groups in each alkyl group is optionally replaced by —O—, —S—, or —N($R^3$)—, provided that no two adjacent methylene groups are both replaced by —O—, —S—, or —N($R^3$)—; and
$R^8$ is a therapeutic agent, detectable label, or biomolecular anchor linked to a solid support; and
Q is —O—, —S—, —N($R^3$)—, —N($R^3$)O—, —ON($R^3$)—, —CH$_2$—, or =NO—.

9. The compound or pharmaceutically acceptable salt thereof of claim 8, of the formula,

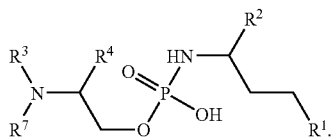

10. The compound or pharmaceutically acceptable salt thereof of claim 9, wherein $R^8$ is a therapeutic agent.

11. The compound or pharmaceutically acceptable salt thereof of claim 10, wherein $R^8$ is a steroidal group optionally substituted with 1 to 5 groups selected from the group consisting of $C_1$-$C_{10}$ alkyl, oxo, hydroxy, or halogen.

12. The compound or pharmaceutically acceptable salt thereof of claim 8 of the formula,

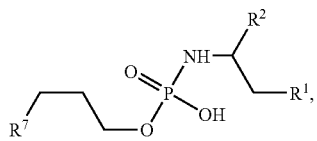

wherein
$R^7$ is —O—$R^8$, wherein
$R^8$ is a steroidal group optionally substituted with 1 to 5 groups selected from the group consisting of $C_1$-$C_{10}$ alkyl, oxo, hydroxy, or halogen.

13. The compound or pharmaceutically acceptable salt thereof of claim 9, wherein $R^8$ is a detectable label.

14. The compound or pharmaceutically acceptable salt thereof of claim 13, wherein $R^8$ is a fluorescent label.

15. The compound or pharmaceutically acceptable salt thereof of claim 14, wherein $R^8$ is a fluorescein or fluorescein derivative.

16. The compound or pharmaceutically acceptable salt thereof of claim 9, wherein $R^8$ is a chelating agent.

17. The compound or pharmaceutically acceptable salt thereof of claim 16, wherein $R^8$ is $R^9$, wherein
$R^9$ is $C_1$-$C_6$ alkyl, aryl, or $C_1$-$C_6$ alkyl-aryl, wherein $R^9$ is substituted with one to three groups which are independently —COOH or N($R^{91}$)$_2$, wherein
each $R^{91}$ is independently —H or $C_1$-$C_6$ alkyl substituted with 1 to 3 groups which are independently —COOH or —N($R^{92}$)$_2$ wherein
each $R^{92}$ is independently —H or $C_1$-$C_6$ alkyl substituted with 1 to 3 COOH.

18. The compound according to claim 8 which is

N-{[(2S)-2-carboxy-2-({4-[({3-[(2-{[3-carboxy-4-(6-hydroxy-3-oxo-9,9a-dihydro-3H-xanthen-9-yl)phenyl]amino}-2-oxoethyl)thio]propanoyl}amino)methyl]benzoyl}amino)ethoxy](hydroxy)phosphoryl}-L-glutamic acid;

N-[{(2S)-2-carboxy-2-[(4-{[(6-{[3-carboxy-4-(6-hydroxy-3-oxo-9,9a-dihydro-3H-xanthen-9-yl)benzoyl]amino}hexanoyl)amino]methyl}benzoyl)amino]ethoxy}(hydroxy)phosphoryl]-L-glutamic acid;

N-{3-[(2-{[3-carboxy-4-(6-hydroxy-3-oxo-9,9a-dihydro-3H-xanthen-9-yl)phenyl]amino}-2-oxoethyl)thio]propanoyl}-L-γ-glutamyl-O-[{[(1S)-1,3-dicarboxypropyl]amino}(hydroxy)phosphoryl]-L-serine;

N-(6-{[3-carboxy-4-(6-hydroxy-3-oxo-9,9a-dihydro-3H-xanthen-9-yl)benzoyl]amino}hexanoyl)-L-γ-glutamyl-O-[{[(1S)-1,3-dicarboxypropyl]amino}(hydroxy)phosphoryl]-L-serine;

N-[{(2S)-2-carboxy-2-[({[3-carboxy-4-(6-hydroxy-3-oxo-9,9a-dihydro-3H-xanthen-9-yl)phenyl]amino}carbonothioyl)amino]ethoxy}(hydroxy)phosphoryl]-L-glutamic acid;

N-{[(4-{2-[bis(carboxymethyl)amino]-3-[{2-[bis(carboxymethyl)amino]ethyl}(carboxymethyl)amino]propyl}phenyl)amino]carbonothioyl}-L-γ-glutamyl-O-[{[(1S)-1,3-dicarboxypropyl]amino}(hydroxy)phosphoryl]-L-serine;

N-{6-[(6-{[5-(2-oxohexahydro-1H-thieno[3,4-d]imidazol-4-yl)pentanoyl]amino}hexanoyl)amino]hexanoyl}-L-γ-glutamyl-O-[{[(1S)-1,3-dicarboxypropyl]amino}(hydroxy)phosphoryl]-L-serine;

N-{[(2S)-2-carboxy-2-({4-[({6-[(6-{[5-(2-oxohexahydro-1H-thieno[3,4-d]imidazol-4-yl)pentanoyl]amino}hexanoyl)amino]hexanoyl}amino)methyl]benzoyl}amino)ethoxy](hydroxy)phosphoryl}-L-glutamic acid;

N-[{3-[(3β,8ξ,9ξ,14ξ,17ξ,20ξ)-cholestan-3-yloxy]propoxy}(hydroxy)phosphoryl]-L-glutamic acid;

N-[hydroxy(3-{[(3β,8ξ,9ξ,14ξ)-17-oxoandrostan-3-yl]oxy}propoxy)phosphoryl]-L-glutamic acid;

N-{[(3β,8ξ,9ξ,14ξ,17ξ,20ξ)-cholestan-3-yloxy](hydroxy)phosphoryl}-L-glutamic acid;

N-(hydroxy{[(3β,8ξ,9ξ,14ξ)-17-oxoandrostan-3-yl]oxy}phosphoryl)-L-glutamic acid;

N-[hydroxy(3-{[17-oxoestra-1(10),2,4-trien-3-yl]oxy}propoxy)phosphoryl]-L-glutamic acid;

N-[(3-{[3-(benzoyloxy)estra-1(10),2,4-trien-17-yl]oxy}propoxy)(hydroxy)phosphoryl]-L-glutamic acid;

or a pharmaceutical acceptable salt thereof.

or a pharmaceutical acceptable salt thereof.

19. A composition comprising a compound according to claim 8 and a pharmaceutically acceptable excipient, carrier, or diluent.

20. A diagnostic kit comprising a compound of claim 8.

* * * * *